US011459284B2

(12) United States Patent
Nair et al.

(10) Patent No.: US 11,459,284 B2
(45) Date of Patent: Oct. 4, 2022

(54) PROCESSES FOR PRODUCING TRIFLUOROIODOMETHANE AND TRIFLUOROACETYL IODIDE

(71) Applicant: Honeywell International Inc., Charlotte, NC (US)

(72) Inventors: Haridasan K. Nair, Williamsville, NY (US); Glenn Matthies, Lockport, NY (US); Rajiv Ratna Singh, Getzville, NY (US); Terris Yang, East Amherst, NY (US); Haiyou Wang, Amherst, NY (US); Ryan J. Hulse, Getzville, NY (US); Rajiv Banavali, Morristown, NJ (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 17/181,479

(22) Filed: Feb. 22, 2021

(65) Prior Publication Data

US 2021/0171423 A1 Jun. 10, 2021

Related U.S. Application Data

(63) Continuation of application No. 16/549,412, filed on Aug. 23, 2019, now Pat. No. 10,954,177.

(Continued)

(51) Int. Cl.
*C07C 17/20* (2006.01)
*C07C 17/35* (2006.01)
(Continued)

(52) U.S. Cl.
CPC .............. *C07C 17/20* (2013.01); *B01J 27/224* (2013.01); *C07C 17/35* (2013.01); *C07C 19/16* (2013.01)

(58) Field of Classification Search
CPC ........ C07C 51/46; C07C 51/17; C07C 51/383; C07C 19/16; C07C 21/18; C09K 5/045; C09K 3/30; C09K 2205/32; C09K 5/044
See application file for complete search history.

(56) References Cited

U.S. PATENT DOCUMENTS

| 2,427,116 A | 9/1947 | Barrick |
| 2,441,128 A | 5/1948 | Barrick et al. |

(Continued)

FOREIGN PATENT DOCUMENTS

| CN | 102992943 A | 3/2013 |
| CN | 103045373 A | 4/2013 |

(Continued)

OTHER PUBLICATIONS

Birchall, Michael J., et al. "Cyclopropane Chemistry. Part III. Thermal Decomposition of Some Halogenopolyfluorocyclopropanes." Journal of the Chemical Society, Perkin Transactions 1: Organic and Bio-Organic Chemistry, 16:1773-1779, 1973.

(Continued)

*Primary Examiner* — Jafar F Parsa
(74) *Attorney, Agent, or Firm* — Faegre Drinker Biddle & Reath LLP

(57) ABSTRACT

The present disclosure provides a process for producing trifluoroiodomethane, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a first catalyst at a first reaction temperature from about 25° C. to about 400° C. to produce an intermediate product stream comprising trifluoroacetyl iodide, and reacting the intermediate product stream in the presence of a second catalyst at a second reaction tempera- (Continued)

ture from about 200° C. to about 600° C. to produce a final product stream comprising the trifluoroiodomethane.

12 Claims, 3 Drawing Sheets

Related U.S. Application Data

(60) Provisional application No. 62/889,958, filed on Aug. 21, 2019, provisional application No. 62/835,918, filed on Apr. 18, 2019, provisional application No. 62/722,561, filed on Aug. 24, 2018.

(51) Int. Cl.
*B01J 27/224* (2006.01)
*C07C 19/16* (2006.01)

(56) References Cited

U.S. PATENT DOCUMENTS

| | | | |
|---|---|---|---|
| 2,462,345 A | 2/1949 | Barrick | |
| 2,848,504 A | 8/1958 | Dixon | |
| 2,931,840 A | 4/1960 | Marquis | |
| 2,982,786 A | 5/1961 | McCane | |
| 3,154,382 A | 10/1964 | Gerald | |
| 3,278,264 A | 10/1966 | Robinson et al. | |
| 3,996,299 A | 12/1976 | Fozzard | |
| 3,996,301 A | 12/1976 | Fozzard | |
| 4,086,407 A | 4/1978 | Fozzard | |
| 5,026,499 A | 6/1991 | Merchant | |
| 5,035,830 A | 7/1991 | Merchant | |
| 5,532,411 A | 7/1996 | Braun et al. | |
| 5,574,192 A | 11/1996 | Vanderpuy et al. | |
| 5,892,136 A | 4/1999 | Nagasaki et al. | |
| 6,624,337 B1 | 9/2003 | Manzer et al. | |
| 7,132,578 B1 | 11/2006 | Mukhopadhyay et al. | |
| 7,196,236 B2 | 3/2007 | Mukhopadhyay et al. | |
| 7,674,939 B2 | 3/2010 | Mukhopadhyay et al. | |
| 8,058,486 B2 | 11/2011 | Merkel et al. | |
| 8,084,653 B2 | 12/2011 | Tung et al. | |
| 8,324,436 B2 | 12/2012 | Mukhopadhyay et al. | |
| 8,425,795 B2 | 4/2013 | Nappa et al. | |
| 8,618,340 B2 | 12/2013 | Kopkalli et al. | |
| 8,975,454 B2 | 3/2015 | Merkel et al. | |
| 9,061,957 B2 | 6/2015 | Mukhopadhyay et al. | |
| 9,790,151 B2 | 10/2017 | Banavali et al. | |
| 9,790,152 B2 | 10/2017 | Sharratt et al. | |
| 9,856,193 B2 | 1/2018 | Nair et al. | |
| 10,005,705 B2 | 6/2018 | Nair et al. | |
| 10,071,940 B2 | 9/2018 | Banavali et al. | |
| 10,662,135 B2* | 5/2020 | Jungong | C07C 21/18 |
| 10,752,565 B2* | 8/2020 | Nair | B01J 21/18 |
| 11,208,582 B2* | 12/2021 | Pham | C09K 5/045 |
| 2006/0122440 A1 | 6/2006 | Mukhopadhyay et al. | |
| 2007/0197842 A1 | 8/2007 | Mukhopadhyay et al. | |
| 2008/0058562 A1 | 3/2008 | Petrov et al. | |
| 2009/0068090 A1 | 3/2009 | Cherry | |
| 2009/0099396 A1 | 4/2009 | Mukhopadhyay et al. | |
| 2009/0137852 A1 | 5/2009 | Yang et al. | |
| 2009/0186986 A1 | 7/2009 | Nomura et al. | |
| 2009/0188379 A1 | 7/2009 | Hiza et al. | |
| 2010/0308261 A1 | 12/2010 | Kanbe et al. | |
| 2011/0097529 A1 | 4/2011 | Durali et al. | |
| 2014/0147480 A1 | 5/2014 | Lu et al. | |
| 2014/0179887 A1 | 6/2014 | Lu et al. | |
| 2015/0224470 A1 | 8/2015 | Tung et al. | |
| 2017/0137353 A1 | 5/2017 | Banavali et al. | |
| 2017/0233316 A1 | 8/2017 | Nair et al. | |
| 2020/0062678 A1 | 2/2020 | Nair et al. | |
| 2020/0062679 A1 | 2/2020 | Nair et al. | |
| 2020/0331753 A1 | 10/2020 | Yang et al. | |

FOREIGN PATENT DOCUMENTS

| | | |
|---|---|---|
| JP | 2005-255514 A | 9/2005 |
| JP | 2007-106628 A | 4/2007 |
| JP | 4713895 B2 | 6/2011 |
| JP | 2012-188359 A | 10/2012 |
| KR | 10-2011-0093831 A | 8/2011 |
| WO | 00/75092 A1 | 12/2000 |
| WO | 2006/011868 A1 | 2/2006 |
| WO | 2009/003085 A1 | 12/2008 |
| WO | 2010/055146 A2 | 5/2010 |
| WO | 2017/083318 A1 | 5/2017 |

OTHER PUBLICATIONS

CN-102992943-A, English translation, Mar. 27, 2013, pp. 1-12 (Year: 2013).

Date, H. "Properties of electron swarms in CF3I" Appl. Phys. Lett 95, 101504 (2009) (Year: 2009).

Haszeldine, R. N. (1951). 124. The Reactions of Metallic Salts of Acids with Halogens. Part I. The Reaction of Metal Trifluoroacetates with Iodine, Bromine, and Chlorine. Journal of the Chemical Society, pp. 584-587.

Hauptschein, Murray, et al. "The Thermal Dimerization of Perfluoropropene." Contribution from the Organic Research Department, Pennsalt Chemicals Corp., vol. 80, pp. 842-845, Feb. 20, 1958.

International Search Report and Written Opinion issued in PCT/US2016/061021, dated Jan. 17, 2017, 7 pages.

International Search Report and Written Opinion issued in PCT/US2017/060394, dated Feb. 14, 2018, 11 pages.

International Search Report and Written Opinion received for PCT Patent Application No. PCT/US2019/047814, dated Dec. 11, 2019, 7 pages.

International Search Report and Written Opinion received for PCT Patent Application No. PCT/US2019/047815, dated Dec. 11, 2019, 7 pages.

International Search Report and Written Opinion received for PCT Patent Application No. PCT/US2020/028437, dated Jul. 28, 2020, 9 pages.

Placzek, D. W. and Rabinovitch, B.S. "The Thermal Isomerization of Trifluoromethyl- and Trifluoroethylcyclopropane." The Journal of Physical Chemistry, 69(7):2141-2145, Jul. 2015, 1965.

Sakaino, Yoshiko. "Structures and Chromotropic Properties of Imadazole Derivatives Produced from 3,6-Bis(4,5-diphenyl-2H-imidazol-2-ylidene)cyclohexa-1,4-diene."J. Chem. Soc. Perkin Trans. I, pp. 1063-1066, 1983.

Solvay Solexis, Via S. Pietro. "2Pi Plus 2Pi Cycloaddition Kinetics of Some Fluoro Olefins and Fluoro Vinyl Ethers." Elsevier, Journal of Fluorine Chemistry, 125:1519-1528, 2004.

Stoiljkovich, D. and Jovanovich, S. "The Mechanism of the High-Pressure Free Radical Polymerization of Ethylene." Journal of Polymer Science: Polymer Chemistry Edition, vol. 19, 741-747, 1981.

Wikipedia "Atmosphere of Earth", pp. 1-14.

* cited by examiner

PROCESSES FOR PRODUCING TRIFLUOROIODOMETHANE AND TRIFLUOROACETYL IODIDE

CROSS-REFERENCE TO RELATED APPLICATIONS

The present application is a U.S. Continuation Application of U.S. application Ser. No. 16/549,412, entitled PROCESSES FOR PRODUCING TRIFLUOROIODOMETHANE AND TRIFLUOROACETYL IODIDE, filed Aug. 23, 2019, which claims the benefit under 35 U.S.C. § 119(e) of U.S. Provisional Patent Application No. 62/889,958, entitled PROCESSES FOR PRODUCING TRIFLUOROIODOMETHANE AND TRIFLUOROACETYL IODIDE, filed on Aug. 21, 2019, U.S. Provisional Patent Application No. 62/835,918, entitled PROCESSES FOR PRODUCING TRIFLUOROIODOMETHANE AND TRIFLUOROACETYL IODIDE, filed on Apr. 18, 2019, and U.S. Provisional Patent Application No. 62/722,561, entitled PROCESSES FOR PRODUCING TRIFLUOROIODOMETHANE AND TRIFLUOROACETYL IODIDE, filed on Aug. 24, 2018, the entire disclosures of which are expressly incorporated herein.

FIELD

The present disclosure relates to processes for producing trifluoroiodomethane ($CF_3I$) and trifluoroacetyl iodide ($CF_3COI$). Specifically, the present disclosure relates to gas-phase processes for producing trifluoroiodomethane and trifluoroacetyl iodide.

BACKGROUND

Trifluoroacetyl iodide ($CF_3COI$) is a compound that can be converted to trifluoroiodomethane ($CF_3I$). Trifluoroiodomethane ($CF_3I$), also known as perfluoromethyliodide, trifluoromethyl iodide, or iodotrifluoromethane, is a useful compound in commercial applications as a refrigerant or a fire suppression agent, for example. Trifluoroiodomethane is a low global warming potential molecule with negligible ozone depletion potential. Trifluoroiodomethane can replace more environmentally damaging materials.

Methods of preparing trifluoroacetyl iodide are known. For example, the article, "The Reactions of Metallic Salts of Acids with Halogens. Part I. The Reaction of Metal Trifluoroacetates with Iodine, Bromine, and Chlorine," R. N. Haszeldine, Journal of the Chemical Society, pp. 584-587 (1951), describes a batch reaction of trifluoroacetyl chloride and anhydrous hydrogen iodide without a catalyst for 8 hours at 120° C. to produce trifluoroacetyl iodide at a yield of about 62%. The poor yield and lengthy reaction times make it quite inefficient.

U.S. Pat. No. 7,196,236 (Mukhopadhyay et al.) discloses a catalytic process for producing trifluoroiodomethane using reactants comprising a source of iodine, at least a stoichiometric amount of oxygen, and a reactant $CF_3R$, where R is selected from the group consisting of —COOH, —COX, —CHO, —COOR$_2$, AND —SO$_2$X, where R$_2$ is alkyl group and X is a chlorine, bromine, or iodine. Hydrogen iodide, which may be produced by the reaction, can be oxidized by the at least a stoichiometric amount of oxygen, producing water and iodine for economic recycling.

U.S. Pat. No. 7,132,578 (Mukhopadhyay et al.) also discloses a catalytic, one-step process for producing trifluoroiodomethane from trifluoroacetyl chloride. However, the source of iodine is iodine fluoride (IF). In contrast to hydrogen iodide, iodine fluoride is relatively unstable, decomposing above 0° C. to $I_2$ and $IF_5$. Iodine fluoride may also not be available in commercially useful quantities.

Some known methods of preparing trifluoroacetyl iodide include liquid-phase processes. Liquid-phase processes can require solvents that must be separated out and disposed of. The extra steps required for separation and disposal make the processes less efficient.

Thus, there is a need to develop a more efficient process that may be scaled to produce commercial quantities of trifluoroiodomethane from relatively inexpensive raw materials.

SUMMARY

The present disclosure provides gas-phase processes for producing trifluoroiodomethane ($CF_3I$) and trifluoroacetyl iodide ($CF_3COI$).

In one embodiment, the present invention provides a gas-phase process for producing trifluoroiodomethane. The process comprises providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a first catalyst at a first reaction temperature from about 25° C. to about 400° C. to produce an intermediate product stream comprising trifluoroacetyl iodide, and reacting the intermediate product stream in the presence of a second catalyst at a second reaction temperature from about 200° C. to about 600° C. to produce a final product stream comprising the trifluoroiodomethane.

In another embodiment, the present invention provides a gas-phase process for producing trifluoroacetyl iodide. The process comprises providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, and reacting the reactant stream in the presence of a first catalyst at a reaction temperature from about 25° C. to about 400° C. to produce a product stream comprising the trifluoroacetyl iodide.

In another embodiment, the present invention provides a composition comprising at least 98 wt. % of trifluoroacetyl iodide, and from about 1 ppm to about 20,000 ppm (about 2 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

In another embodiment, the present invention provides a composition comprising at least 99 wt. % of trifluoroiodomethane, from 1 ppm to 500 ppm chlorotrifluoroethane, less than 500 ppm hexafluoroethane, less than 500 ppm trifluoromethane, less than 100 ppm carbon monoxide, less than 1 ppm hydrogen chloride and from 1 ppm to 500 ppm in total of compounds selected from the group consisting of trifluoroacetyl fluoride, hexafluoropropanone, trifluoroacetaldehyde, and trifluoroacetyl chloride.

In another embodiment, the present invention provides a gas-phase process for producing trifluoroiodomethane. The process comprises providing a reactant stream comprising trifluoroacetyl iodide, and reacting the reactant stream in the presence of a catalyst at a reaction temperature from about 200° C. to about 600° C. to produce a product stream comprising the trifluoroiodomethane.

The above mentioned and other features of the disclosure, and the manner of attaining them, will become more apparent and will be better understood by reference to the following description of embodiments taken in conjunction with the accompanying drawings.

DETAILED DESCRIPTION

Figure 1:
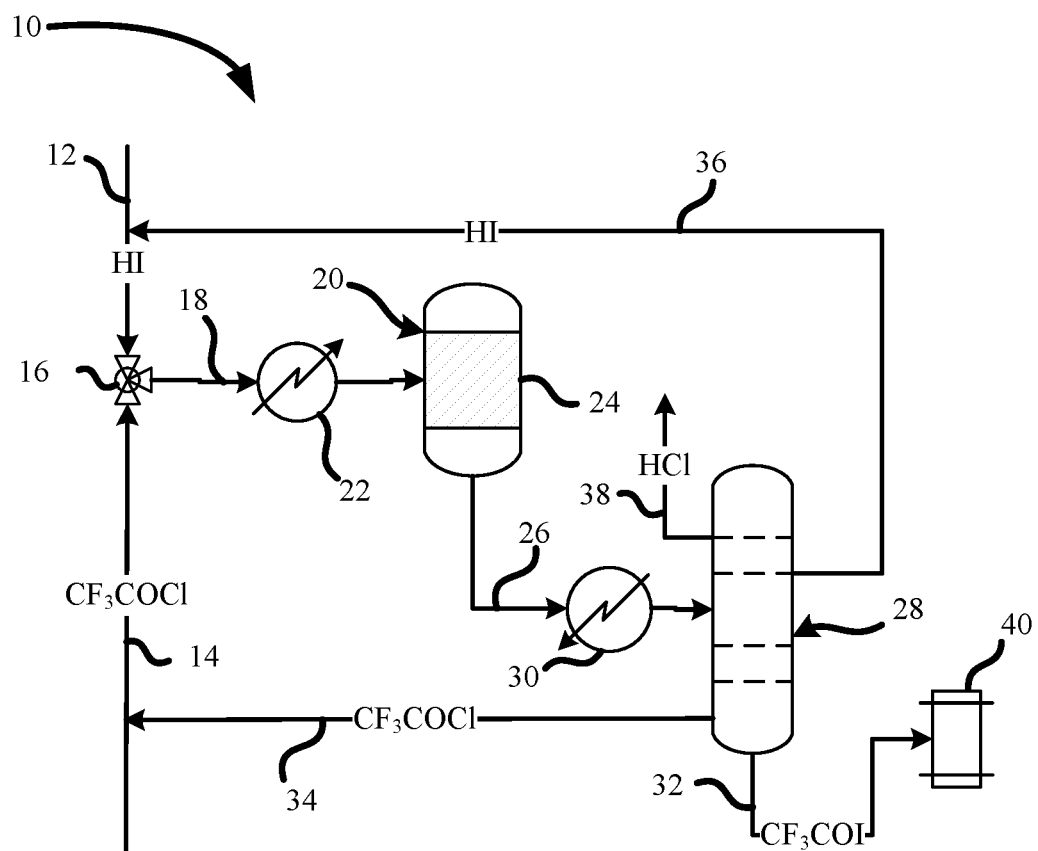
FIG. 1 is a process flow diagram showing a gas-phase process for manufacturing trifluoroacetyl iodide.

The present disclosure provides processes for the manufacture of trifluoroiodomethane and trifluoroacetyl iodide that produce surprisingly good process yields starting from hydrogen, iodine, and a trifluoroacetyl halide, such as trifluoroacetyl chloride. Such starting materials are relatively inexpensive and readily available in commercial quantities. The processes of this disclosure may be high-yielding, gas-phase processes that are amenable for the manufacture of trifluoroiodomethane and trifluoroacetyl iodide on a commercial scale. The disclosed gas-phase processes require no solvents, further enhancing their commercial appeal.

As disclosed herein, the trifluoroiodomethane and trifluoroacetyl iodide are produced from a reactant stream comprising hydrogen iodide (HI) and trifluoroacetyl halide ($CF_3COX$, X=Cl, Br or F). The hydrogen iodide and the trifluoroacetyl halide are anhydrous. It is preferred that there be as little water in the reactant stream as possible because any water in the reactant stream may hydrolyze some of the trifluoroacetyl halide and form the more thermodynamically favorable trifluoroacetic acid, rather than the desired trifluoroacetyl iodide.

The anhydrous hydrogen iodide is substantially free of water. That is, any water in the anhydrous hydrogen iodide is in an amount by weight less than about 500 parts per million, about 300 ppm, about 200 ppm, about 100 ppm, about 50 ppm, about 30 ppm, about 20 ppm, about 10 ppm, about 5 ppm, about 3 ppm, about 2 ppm, or about 1 ppm, or less than any value defined between any two of the foregoing values. Preferably, the anhydrous hydrogen iodide comprises water by weight in an amount less than about 100 ppm. More preferably, the anhydrous hydrogen iodide comprises water by weight in an amount less than about 10 ppm. Most preferably, the anhydrous hydrogen iodide comprises water by weight in an amount less than about 1 ppm.

The reactant stream is substantially free of oxygen. That is, any oxygen in the reactant stream is in an amount by weight less than about 500 parts per million, about 300 ppm, about 200 ppm, about 100 ppm, about 50 ppm, about 30 ppm, about 20 ppm, about 10 ppm, about 5 ppm, about 3 ppm, about 2 ppm, or about 1 ppm, or less than any value defined between any two of the foregoing values. Preferably, the amount of oxygen by weight in the reactant stream is less than about 100 ppm. More preferably, the amount of oxygen by weight in the reactant stream is less than about 10 ppm. Most preferably, the amount of oxygen by weight in the reactant stream is less than about 1 ppm. It is preferred that there be as little oxygen in the reaction stream as possible because any oxygen in the reaction stream may oxidize at least some of the hydrogen iodide to form iodine and water before the hydrogen iodide can react to form trifluoroacetyl iodide. Even if running with an excess of hydrogen iodide, the water formed may hydrolyze the trifluoroacetyl halide and form the more thermodynamically favorable trifluoroacetic acid, rather than the desired trifluoroiodomethane, reducing the efficiency of the process.

The at least one trifluoroacetyl halide is selected from the group consisting of trifluoroacetyl fluoride ($CF_3COF$), trifluoroacetyl chloride ($CF_3COCl$), trifluoroacetyl bromide ($CF_3COBr$), and any combinations thereof. Preferably, the at least one trifluoroacetyl halide comprises trifluoroacetyl chloride. More preferably, the at least one trifluoroacetyl halide consists essentially of trifluoroacetyl chloride. Most preferably, the at least one trifluoroacetyl halide consists of trifluoroacetyl chloride.

Trifluoroacetyl chloride, for example, is readily available in commercial quantities from Sigma-Aldrich Corp., St. Louis, Mo., Halocarbon Products Corporation, Peachtree Corners, Ga., or from Solvay S.A., Brussels, Belgium, for example. Hydrogen iodide is commercially available or may be manufactured by, for example, reacting elemental iodine with hydrazine, distilling it from a solution of sodium iodide and phosphoric acid, or irradiating a mixture of hydrogen and elemental iodine at a wavelength of about 578 nanometers.

In the reactant stream, a mole ratio of the hydrogen iodide to the trifluoroacetyl halide may be as low as about 0.1:1, about 0.2:1, about 0.3:1, about 0.4:1, about 0.5:1, about 0.6:1, about 0.7:1, about 0.8:1, about 0.9:1, about 0.95:1, about 0.99:1, or about 1:1, or as high as about 1.01:1, about 1.05:1, about 1.1:1, about 1.2:1, about 1.3:1, about 1.4:1, about 1.5:1, about 1.6:1, about 1.8:1, about 2.0:1, about 4.0:1, about 6.0:1, about 8.0:1, or about 10.0:1, or within any range defined between any two of the foregoing values, such as about 0.1:1 to about 10.0:1, about 0.2:1 to about 8.0:1, about 0.3:1 to about 6.0:1, about 0.4:1 to about 4.0:1, 0.5:1 to about 2.0:1, about 0.6:1 to about 1.2:1, about 0.7:1 to about 1.0:1, about 0.1:1 to about 2.0:1, about 0.5:1 to about 1.5:1, about 0.6:1 to about 1.4:1, about 0.7:1 to about 1.3:1, about 0.8:1 to about 1.2:1, about 0.9:1 to about 1.1:1, about 0.95:1 to about 1.05:1, about 0.99:1 to about 1.01:1, about 1:1 to about 2:1, about 0.8:1 to about 1.5:1, or about 0.95:1 to about 1.2:1, for example. Preferably, the mole ratio of the hydrogen iodide to the trifluoroacetyl halide may be from about 0.5:1 to about 2.0:1. More preferably, the mole ratio of the hydrogen iodide to the trifluoroacetyl halide may be from about 0.6:1 to about 1.2:1. Most preferably, the mole ratio of the hydrogen iodide to the trifluoroacetyl halide may be from about 0.7:1 to about 1.0:1.

The trifluoroacetyl halide and the hydrogen iodide forming the reactant stream may be individually pre-heated or pre-heated together before entering the reactor. The reactant stream may be pre-heated to a temperature as low as about 20° C., about 30° C., about 40° C., about 50° C., about 60° C., or about 70° C., or to a temperature as high as about 80° C., about 90° C., about 100° C., about 110° C., or about 120° C., or to a temperature within any range defined between any two of the foregoing values, such as about 30° C. to about 120° C., about 40° C. to about 110° C., about 50° C. to about 100° C., about 60° C. to about 90° C., or about 70° C. to about 80° C., for example. Preferably, the reactant stream may be pre-heated to a temperature from about 40° C. to about 120° C. More preferably, the reactant stream may be pre-heated to a temperature from about 60° C. to about 110° C. Most preferably, the reactant stream may be pre-heated to a temperature from about 80° C. to about 100° C.

The hydrogen iodide and the trifluoroacetyl halide in the reactant stream react within a first reactor to produce an intermediate product stream comprising trifluoroacetyl iodide ($CF_3COI$) and at least one hydrogen halide (HX) by-product according to Equation 1 below:

$$HI + CF_3COX \rightarrow CF_3COI + HX. \qquad \text{Eq. 1:}$$

The at least one hydrogen halide is selected from the group consisting of hydrogen fluoride (HF), hydrogen chloride (HCl), and hydrogen bromide (HBr).

The first reactor may be a heated tube reactor comprising a tube made of a metal such as stainless steel, nickel, and/or a nickel alloy, such as a nickel-chromium alloy, a nickel-molybdenum alloy, a nickel-chromium-molybdenum alloy, or a nickel-copper alloy. The tube within the first reactor may be heated. The first reactor may be any type of packed bed reactor.

The hydrogen iodide and the trifluoroacetyl halide in the reactant stream reacts in the presence of a first catalyst contained within the first reactor. The first catalyst may comprise activated carbon, meso carbon, stainless steel, nickel, nickel-chromium alloy, nickel-chromium-molybdenum alloy, nickel-copper alloy, copper, alumina, platinum, palladium, or carbides, such as metal carbides, such as iron carbide, molybdenum carbide and nickel carbide, and non-metal carbides, such as silicon carbide, or combinations thereof. The first catalyst may be in the form of a mesh, pellet, or sphere, contained within the first reactor. The first catalyst may have an average diameter ranging from about 1 mm to about 25 mm.

If the first catalyst comprises platinum and/or palladium, the first catalyst may be in the form of platinum and/or palladium on a support. The support for the first catalyst may comprise alumina or carbon. The amount of platinum and/or palladium on the support, as a percentage of the total combined weight of the platinum and/or palladium and the support may be as little as about 0.01 weight percent (wt. %), about 0.1 wt. %, about 0.3 wt. %, about 0.5 wt. %, about 0.7 wt. %, about 1 wt. %, about 2 wt. %, or about 3 wt. % or as great as about 4 wt. %, about 5 wt. %, about 6 wt. %, about 8 wt. %, or about 10 wt. %, or within any range defined between any two of the foregoing values, such as about 0.01 wt. % to about 10 wt. %, about 0.1 wt. % to about 10 wt. %, about 0.5 wt. % to about 8 wt. %, about 1 wt. % to about 6 wt. %, about 2 wt. % to about 5 wt. %, about 3 wt. % to about 4 wt. %, about 2 wt. % to about 3 wt. %, or about 0.5 wt. % to about 5 wt. %, for example. Preferably, the amount of platinum and/or palladium on the support may be from about 0.1 wt. % to about 1 wt. %. More preferably, the amount of platinum and/or palladium on the support may be from about 0.3 wt. % to about 0.7 wt. %. Most preferably, the amount of platinum and/or palladium on the support may be about 0.5 wt. %.

Preferably, the first catalyst comprises activated carbon, meso carbon, stainless steel, platinum on a support, palladium on a support, or carbides, such as metal carbides and non-metal carbides, such as silicon carbide, or combinations thereof. More preferably, the first catalyst comprises platinum on a support, palladium on a support, activated carbon, silicon carbide, or combinations thereof. Most preferably, the first catalyst comprises activated carbon or silicon carbide.

Alternatively, the first catalyst may consist of surfaces of the first reactor itself in contact with the reactant stream. The surfaces may provide a catalytic effect without the need for an additional catalyst.

The reactant stream may be in contact with the first catalyst for a contact time as short as about 0.1 seconds, 0.5 seconds, about 1 second, about 2 seconds, about 3 seconds, about 5 seconds, about 8 seconds, about 10 seconds, about 12 seconds, or about 15, about 18 seconds, or as long as about 20 seconds, about 25 seconds, about 30 seconds, about 35 seconds, about 40 seconds, about 50 seconds, about 60 seconds, about 80 seconds, or about 300 seconds, or for any contact time within any range defined between any two of the foregoing values, such as about 0.1 seconds to about 300 seconds, about 0.5 seconds to about 80 seconds, about 1 second to about 60 seconds, about 5 seconds to about 50 seconds, about 8 seconds to about 40 seconds, about 10 seconds to about 35 seconds, about 12 seconds to about 30 seconds, about 15 seconds to about 25 seconds, about 18 seconds to about 20 seconds, about 10 seconds to about 40 seconds, or about 10 seconds to about 30 seconds, for example. Preferably, the reactant stream may be in contact with the first catalyst for a contact time from about 5 seconds to about 60 seconds. More preferably, the reactant stream may be in contact with the first catalyst for a contact time from about 10 seconds to about 40 seconds. Most preferably, the reactant stream may be in contact with the first catalyst for a contact time from about 15 seconds to about 35 seconds.

The reaction may be maintained at a first reaction operating pressure as low as about atmospheric pressure, about 5 psig (34 kPaG), about 10 psig (69 kPaG), about 15 psig (103 kPaG), about 20 psig (138 kPaG), about 25 psig (172 kPaG), about 30 psig (207 kPaG), about 35 psig (241 kPaG), or about 40 psig (276 kPaG), or as high as about 50 psig (345 kPaG), about 60 psig (414 kPaG), about 70 psig (483 kPaG), about 80 psig (552 kPaG), about 100 psig (689 kPaG), about 150 psig (1,034 kPaG), about 200 psig (1,379 kPaG), about 250 psig (1,724 kPaG), or about 300 psig (2,068 KPaG), or within any range defined between any two of the foregoing values, such as about atmospheric pressure to about 300 psig (2,068 KPaG), about 5 psig (34 kPaG) to about 250 psig (1,724 kPaG), about 10 psig (69 kPaG) to about 200 psig (1,379 kPaG), about 15 psig (103 kPaG) to about 150 psig (1,034 kPaG), about 20 psig (138 kPaG) to about 100 psig (689 kPaG), about 25 psig (172 kPaG) to about 80 psig (552 kPaG), about 30 psig (207 kPaG) to about 70 psig (483 kPaG), about 35 psig (241 kPaG) to about 60 psig (414 kPaG), about 40 psig (276 kPaG) to about 50 psig (345 kPaG), or about 140 kPaG to about 200 kPaG, for example. Preferably, the first reaction operation pressure is from about 5 psig (34 kPaG) to about 200 psig (1,379 kPaG). More preferably, the first reaction operating pressure is from about 10 psig (69 kPaG) to about 150 psig (1,034 kPaG). Most preferably, the first reaction operating pressure is from about 20 psig (138 kPaG) to about 100 psig (689 kPaG).

In addition to trifluoroacetyl iodide and hydrogen halide, the intermediate product stream further comprises unreacted trifluoroacetyl halide and hydrogen iodide. The intermediate product stream may further comprise small amounts of other organic compounds, such as trifluoroiodomethane ($CF_3I$), for example.

The composition of the organic compounds in the intermediate product stream may be measured as by gas chromatography (GC) and gas chromatography-mass spectroscopy (GC-MS) analyses. Peak areas provided by the GC analysis for each of the organic compounds can be combined to provide a GC area percentage (GC area %) of the total organic compounds for each of the organic compounds as a measurement of the relative concentrations of the organic compounds in the intermediate product stream. The GC area % may be interpreted as equivalent to a weight %.

The concentration of unreacted trifluoroacetyl halide in the intermediate product stream, in GC area % of total organic compounds, may be as low as about 1%, about 3%, about 5%, about 10%, about 15%, about 20%, about 25%, about 30%, about 35%, about 40%, or about 45%, or may be as high as about 50%, about 55%, about 60%, about 65%, about 70%, about 75%, about 80%, about 85%, or about 90%, or within any range defined between any two of the foregoing values, such as about 1% to about 90%, about 5% to about 85%, about 10% to about 80%, about 15% to about 75%, about 20% to about 70%, about 25% to about 65%, about 30% to about 60%, about 35% to about 55%, about 40% to about 50%, about 1% to about 3%, about 5% to about 40% or about 5% to about 60%, for example. Preferably, the concentration of unreacted trifluoroacetyl halide in the intermediate product stream may be from about 1% to about 50%. More preferably, the concentration of unreacted trifluoroacetyl halide in the intermediate product stream may be from about 1% to about 40%. Most preferably, the concentration of unreacted trifluoroacetyl halide in the intermediate product stream may be from about 1% to about 30%.

The concentration of organic compounds in the intermediate product stream excluding trifluoroacetyl halide, trifluoroacetyl iodide and trifluoroiodomethane, in GC area % of total organic compounds, may be less than about 15%, about 14%, about 13%, about 12%, about 11%, about 10%, about 9%, about 8%, about 7%, about 6%, about 5%, about 4%, about 3%, about 2%, about 1%, about 0.5%, or about 0.1%. Preferably, the concentration of all other organic compounds in the intermediate product stream may be less than about 8%. More preferably, the concentration of all other organic compounds in the intermediate product stream may be less than about 4%. Most preferably, the concentration of all other organic compounds in the intermediate product stream may be less than about 2%.

The reaction stream may be heated to a first reaction temperature as low as about 25° C., about 30° C., about 40° C., about 50° C., about 60° C., about 70° C., about 80° C., about 90° C., about 100° C., or about 120° C., or as high as about 150° C., about 180° C., about 200° C., about 220° C., about 230° C., about 250° C., about 300° C., about 360° C., or about 400° C. or to a first reaction temperature within any range defined between any two of the foregoing values, such as about 25° C. to about 400° C., about 30° C. to about 360° C., about 40° C. to about 300° C., about 50° C. to about 280° C., about 60° C. to about 250° C., about 70° C. to about 230° C., about 80° C. to about 220° C., about 90° C. to about 200° C., about 100° C. to about 180° C., or about 110° C. to about 150° C., for example.

In general, the conversion of trifluoroacetyl halide can be controlled through the selection of the catalyst, the first reaction temperature, the mole ratio of the hydrogen iodide to the trifluoroacetyl halide, and the contact time.

Although the reaction can be carried out at a first reaction temperature from about 25° C. to about 400° C., it has been found that a lower reaction temperature, such as a first reaction temperature at or below about 120° C., the reaction can produce a low concentration of trifluoroiodomethane in the intermediate product stream. Although trifluoroiodomethane can be the final product desired, the presence of trifluoroiodomethane in the intermediate product stream can reduce the overall efficiency of the process because the trifluoroiodomethane can form an azeotrope with the trifluoroacetyl halide, such as trifluoroacetyl chloride, for example. The azeotrope can make it difficult to separate the trifluoroiodomethane from the trifluoroacetyl chloride, resulting in the loss of the trifluoroiodomethane.

It has been found that at first reaction temperatures at or below about 120° C., a concentration of trifluoroiodomethane in the intermediate product stream can be less than 0.002%, or about 20 ppm, of the total organic compounds. For less than about 0.002% GC area % of trifluoroiodomethane in the intermediate product stream, the reaction stream may be heated to a first reaction temperature as low as about 25° C., about 30° C., about 35° C., about 40° C., about 45° C., about 50° C., about 55° C., about 60° C., about 65° C., or about 70° C., or to a temperature as high as about 75° C., about 80° C., about 85° C., about 90° C., about 95° C., about 100° C., about 105° C., about 110° C., about 115° C. or about 120° C. or to a first reaction temperature within any range defined between any two of the foregoing values, such as about 25° C. to about 120° C., about 30° C. to about 115° C., about 35° C. to about 110° C., about 40° C. to about 105° C., about 45° C. to about 100° C., about 50° C. to about 95° C., about 55° C. to about 90° C., about 60° C. to about 85° C., about 65° C. to about 80° C. or about 70° C. to about 75° C., for example. Preferably, the reaction stream may be heated to a first reaction temperature from about 40° C. to about 120° C. More preferably, the reaction stream may be heated to a first reaction temperature from about 70° C. to about 100° C. Most preferably, the reaction stream may be heated to a first reaction temperature from about 80° C. to about 100° C.

The concentration of trifluoroacetyl iodide in the intermediate product stream, in GC area % of total organic compounds, where the reaction stream has a reaction temperature at or below about 120° C., may be as low as about 10%, about 20%, about 30%, about 35%, about 40%, about 45%, about 50%, about 55%, about 60%, about 65% or about 70%, or may be as high as about 75%, about 80%, about 85%, about 90%, about 95%, about 97%, about 98%, or about 99% or within any range defined between any two of the foregoing values, such as about 10% to about 99%, about 10% to about 99%, about 30% to about 99%, about 35% to about 98%, about 40% to about 97%, about 45% to about 95%, about 50% to about 90%, about 55% to about 85%, about 60% to about 80%, about 65% to about 75%, about 50% to about 60%, about 90% to about 99% or about 95% to about 99%, for example. Preferably, the concentration of trifluoroacetyl iodide in the intermediate product stream may be from about 50% to about 99%. More preferably, the concentration of trifluoroacetyl iodide in the intermediate product stream may be from about 60% to about 99%. Most preferably, the concentration of trifluoroacetyl iodide in the intermediate product stream may be from about 70% to about 99%.

The concentration of trifluoroiodomethane in the intermediate product stream, in GC area % of total organic compounds, where the reaction stream has a reaction temperature at or below about 120° C., may be less than about 0.010%, less than about 0.005%, less than about 0.002%, less than about 0.001%, less than about 0.0005%, less than about 0.0002%, or less than about 0.0001%, or less than any value defined between any two of the foregoing values. Preferably, the concentration of trifluoroiodomethane in the intermediate product stream may be less than about 0.002%. More preferably, the concentration of trifluoroiodomethane in the intermediate product stream may be less than about 0.001%. Most preferably, the concentration of trifluoroiodomethane in the intermediate product stream may be less than about 0.0005%.

Alternatively stated, organic compounds in the intermediate product stream, where the reaction stream has a first reaction temperature at or below about 120° C., may comprise, in GC area % of total organic compounds, from about 10% to about 99% trifluoroacetyl iodide, from about 1% to about 90% unreacted trifluoroacetyl halide, less than about 0.010% trifluoroiodomethane, and less than about 15% organic compounds other than trifluoroacetyl iodide, trifluoroacetyl halide, and trifluoroiodomethane. It is also provided that organic compounds in the intermediate product stream may comprise from about 50% to about 99% trifluoroacetyl iodide, from about 1% to about 50% unreacted trifluoroacetyl halide, less than about 0.002% trifluoroiodomethane, and less than about 8% organic compounds other than trifluoroacetyl iodide, trifluoroacetyl halide, and trifluoroiodomethane. It is also provided that organic compounds in the intermediate product stream may comprise from about 60% to about 99% trifluoroacetyl iodide, from about 1% to about 40% unreacted trifluoroacetyl halide, less than about 0.001% trifluoroiodomethane, and less than about 4% organic compounds other than trifluoroacetyl iodide, trifluoroacetyl halide, and trifluoroiodomethane. It is also provided that organic compounds in the intermediate product stream may comprise from about 70% to about 99% trifluoroacetyl iodide, from about 1% to about 30% unreacted trifluoroacetyl halide, less than about 0.0005% trifluoroiodomethane, and less than about 2% organic compounds other than trifluoroacetyl iodide, trifluoroacetyl halide, and trifluoroiodomethane.

Alternatively stated, organic compounds in the intermediate product stream, where the reaction stream has a first reaction temperature at or below about 120° C., may consist essentially of, in GC area % of total organic compounds, from about 10% to about 99% trifluoroacetyl iodide, from about 1% to about 90% unreacted trifluoroacetyl halide, less than about 0.010% trifluoroiodomethane, and less than about 15% organic compounds other than trifluoroacetyl iodide, trifluoroacetyl halide, and trifluoroiodomethane. It is also provided that organic compounds in the intermediate product stream may consist essentially of from about 50% to about 99% trifluoroacetyl iodide, from about 1% to about 50% unreacted trifluoroacetyl halide, less than about 0.002% trifluoroiodomethane, and less than about 8% organic compounds other than trifluoroacetyl iodide, trifluoroacetyl halide, and trifluoroiodomethane. It is also provided that organic compounds in the intermediate product stream may consist essentially of from about 60% to about 99% trifluoroacetyl iodide, from about 1% to about 40% unreacted trifluoroacetyl halide, less than about 0.001% trifluoroiodomethane, and less than about 4% organic compounds other than trifluoroacetyl iodide, trifluoroacetyl halide, and trifluoroiodomethane. It is also provided that organic compounds in the intermediate product stream may consist essentially of from about 70% to about 99% trifluoroacetyl iodide, from about 1% to about 30% unreacted trifluoroacetyl halide, less than about 0.0005% trifluoroiodomethane, and less than about 2% organic compounds other than trifluoroacetyl iodide, trifluoroacetyl halide, and trifluoroiodomethane.

Alternatively stated, organic compounds in the intermediate product stream, where the reaction stream has a first reaction temperature at or below about 120° C., may consist of, in GC area % of total organic compounds, from about 10% to about 99% trifluoroacetyl iodide, from about 1% to about 90% unreacted trifluoroacetyl halide, less than about 0.010% trifluoroiodomethane, and less than about 15% organic compounds other than trifluoroacetyl iodide, trifluoroacetyl halide, and trifluoroiodomethane. It is also provided that organic compounds in the intermediate product stream may consist of from about 50% to about 99% trifluoroacetyl iodide, from about 1% to about 50% unreacted trifluoroacetyl halide, less than about 0.002% trifluoroiodomethane, and less than about 8% organic compounds other than trifluoroacetyl iodide, trifluoroacetyl halide, and trifluoroiodomethane. It is also provided that organic compounds in the intermediate product stream may consist of from about 60% to about 99% trifluoroacetyl iodide, from about 1% to about 40% unreacted trifluoroacetyl halide, less than about 0.001% trifluoroiodomethane, and less than about 4% organic compounds other than trifluoroacetyl iodide, trifluoroacetyl halide, and trifluoroiodomethane. It is also provided that organic compounds in the intermediate product stream may consist of from about 70% to about 99% trifluoroacetyl iodide, from about 1% to about 30% unreacted trifluoroacetyl halide, less than about 0.0005% trifluoroiodomethane, and less than about 2% organic compounds other than trifluoroacetyl iodide, trifluoroacetyl halide, and trifluoroiodomethane.

The intermediate product stream may proceed directly to a first distillation column. Alternatively, the intermediate product stream may pass through a heat exchanger to cool the intermediate product stream before the intermediate product stream is provided to the first distillation column.

The first distillation column is configured for the separation of some of the by-products, reactants, and organic compounds described above from the trifluoroacetyl iodide to produce a purified intermediate product stream. The first distillation column may be configured to separate and return the unreacted hydrogen iodide to the reactant stream and to separate and return the unreacted trifluoroacetyl halide to the reactant stream. The first distillation column may also be configured to separate the hydrogen halide into a hydrogen halide stream for sale, reuse elsewhere, or disposal. The first distillation column may include a series of distillation columns, such as a hydrogen halide column to remove the hydrogen halide and light organics, a lights column to remove the unreacted trifluoroacetyl halide and the unreacted hydrogen iodide before sending them to a recycle column to separate the unreacted trifluoroacetyl halide from the unreacted hydrogen iodide, and a heavies column to purge heavy organics and produce the purified intermediate product stream.

The concentration of the trifluoroacetyl iodide in the purified intermediate product stream may be greater than about 98 weight percent (wt. %). Preferably, the concentration of the trifluoroacetyl iodide in the purified intermediate product stream may be greater than about 99 wt. %. More preferably, the concentration of the trifluoroacetyl iodide in the purified intermediate product stream may be greater than about 99.5 wt. %. Most preferably, the concentration of the trifluoroacetyl iodide in the purified intermediate product stream may be greater than about 99.7 wt. %.

The concentration of some impurities in the purified intermediate product stream may detract from the further use of the trifluoroacetyl iodide. Thus, if the trifluoroacetyl halide in the reactant stream includes trifluoroacetyl chloride, the purified intermediate product stream includes from about 1 ppm (part per million by weight) to about 20,000 ppm (about 2 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. Preferably, the purified intermediate product stream includes from about 1 ppm to about 10,000 ppm (about 1 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. More preferably, the purified intermediate product stream includes from about 1 ppm to about 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. Most preferably, the purified intermediate product stream includes from about 1 ppm to about 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Alternatively stated, the purified intermediate product stream may comprise at least 98 wt. % of trifluoroacetyl iodide, and from about 1 ppm to about 20,000 ppm (about 2 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may comprise at least 99 wt. % of trifluoroacetyl iodide, and from 1 ppm to 10,000 ppm (1 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may comprise at least 99.5 wt. % of trifluoroacetyl iodide, and from 1 ppm to 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may comprise at least 99.7 wt. % of trifluoroacetyl iodide, and from 1 ppm to 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Alternatively stated, the purified intermediate product stream may consist essentially of at least 98 wt. % of trifluoroacetyl iodide, and from about 1 ppm to about 20,000 ppm (about 2 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may consist essentially of at least 99 wt. % of trifluoroacetyl iodide, and from 1 ppm to 10,000 ppm (1 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may consist essentially of at least 99.5 wt. % of trifluoroacetyl iodide, and from 1 ppm to 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may consist essentially of at least 99.7 wt. % of trifluoroacetyl iodide, and from 1 ppm to 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Alternatively stated, the purified intermediate product stream may consist of at least 98 wt. % of trifluoroacetyl iodide, and from about 1 ppm to about 20,000 ppm (about 2 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may consist of at least 99 wt. % of trifluoroacetyl iodide, and from 1 ppm to 10,000 ppm (1 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may consist of at least 99.5 wt. % of trifluoroacetyl iodide, and from 1 ppm to 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane. It is also provided that the purified intermediate product stream may consist of at least 99.7 wt. % of trifluoroacetyl iodide, and from 1 ppm to 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

The purified intermediate product stream may be stored, or may be provided to a second reactor for conversion into trifluoroiodomethane. The purified intermediate product stream comprising the trifluoroacetyl iodide may be provided directly to the second reactor. Alternatively, or additionally, the purified intermediate product stream may pass through a preheater to heat the purified intermediate product stream before the purified intermediate product stream is provided to the second reactor.

The trifluoroacetyl iodide in the purified intermediate product stream reacts within the second reactor to produce a final product stream comprising trifluoroiodomethane and reaction by-product carbon monoxide (CO) according to Equation 2 below:

$$CF_3COI \rightarrow CF_3I + CO. \qquad \text{Eq. 2:}$$

The second reactor may be a heated tube reactor comprising a tube made of a metal such as stainless steel, nickel, and/or a nickel alloy, such as a nickel-chromium alloy, a nickel-molybdenum alloy, a nickel-chromium-molybdenum alloy, or a nickel-copper alloy. The tube within the second reactor may be heated. The second reactor may be any type of packed bed reactor.

The purified intermediate product stream may be heated to a second reaction temperature as low as about 200° C., about 250° C., about 300° C., about 310° C., about 320° C., about 325° C., about 330° C., about 340° C., about 350° C., or about 360° C., or to a second reaction temperature as high as about 370° C., about 380° C., about 390° C., about 400° C., about 425° C., about 450° C., about 475° C., about 500° C., about 525° C., about 550° C., about 575° C., or about 600° C. or any range defined between any two of the foregoing values, such as about 200° C. to about 600° C., about 250° C. to about 600° C., about 300° C. to about 600° C., about 320° C. to about 450° C., about 325° C. to about 400° C., about 330° C. to about 390° C., about 340° C. to about 380° C., about 350° C. to about 370° C., or about 340° C. to about 360° C., for example. Preferably, the second catalyst may be heated to a second reaction temperature from about 250° C. to about 500° C. More preferably, the second catalyst may be heated to a second reaction temperature from about 300° C. to about 400° C. Most preferably, the second catalyst may be heated to a second reaction temperature from about 300° C. to about 350° C.

The trifluoroacetyl iodide in the purified intermediate product stream may react in the presence of a second catalyst contained within the second reactor. The second catalyst may comprise stainless steel, nickel, nickel-chromium alloy, nickel-chromium-molybdenum alloy, nickel-copper alloy, copper, alumina, silicon carbide, platinum, palladium, rhenium, activated carbon, such as such as Norit-PK35, Calgon or Shirasagi carbon, or combinations thereof. The second catalyst may be in the form of a mesh, pellet, or sphere, contained within the second reactor. The second catalyst may have an average diameter ranging from about 1 mm to about 25 mm.

If the second catalyst comprises platinum, palladium, and/or rhenium, the second catalyst may be in the form of platinum, palladium, and/or rhenium on a support.

The support for the second catalyst may comprise alumina or carbon. The amount of platinum, palladium, and/or rhenium on the support, as a percentage of the total combined weight of the platinum, palladium, and/or rhenium and the support may be as little as about 0.01 weight percent (wt. %), about 0.1 wt. %, about 0.3 wt. %, about 0.5 wt. %, about 0.7 wt. %, about 1 wt. %, about 2 wt. %, or about 3 wt. % or as great as about 4 wt. %, about 5 wt. %, about 6 wt. %, about 8 wt. %, or about 10 wt. %, or within any range defined between any two of the foregoing values, such as about 0.01 wt. % to about 10 wt. %, 0.1 wt. % to about 10 wt. %, about 0.5 wt. % to about 8 wt. %, about 1 wt. % to about 6 wt. %, about 2 wt. % to about 5 wt. %, about 3 wt. % to about 4 wt. %, about 2 wt. % to about 3 wt. %, or about 0.5 wt. % to about 5 wt. %, for example. Preferably, the amount of platinum, palladium, and/or rhenium on the support may be from about 0.1 wt. % to about 1 wt. %. More preferably, the amount of platinum, palladium, and/or rhenium on the support may be from about 0.3 wt. % to about 0.7 wt. %. Most preferably, the amount of platinum, palladium, and/or rhenium on the support may be about 0.5 wt. %.

Preferably, the second catalyst comprises activated carbon, about 0.1 wt. % to about 1 wt. % platinum on a support, about 0.1 wt. % to about 1 wt. % palladium on a support, about 0.1 wt. % to about 1 wt. % rhenium on a support, or combinations thereof. More preferably, the second catalyst comprises activated carbon or about 0.3 wt. % to about 0.7 wt. % palladium on a support. Most preferably, the second catalyst comprises activated carbon.

The second catalyst may be an activated carbon, such as Norit-PK35, Calgon or Shirasagi carbon pellets or spheres, for example. The activated carbon may have a surface area as small as about 500 square meters per gram ($m^2/g$), about 800 $m^2/g$, about 850 $m^2/g$, about 900 $m^2/g$, about 950 $m^2/g$, or about 1,000 $m^2/g$, or as large as about 1,100 $m^2/g$, about 1,200 $m^2/g$, about 1,300 $m^2/g$, about 1,400 $m^2/g$, about 1,600 $m^2/g$, about 1,800 $m^2/g$, about 2,000 $m^2/g$, or about 3,000 $m^2/g$, or have a surface area within any range defined between any two of the foregoing values, such as about 500 $m^2/g$ to about 3,000 $m^2/g$, about 800 $m^2/g$ to about 2,000 $m^2/g$, about 850 $m^2/g$ to about 1,800 $m^2/g$, about 900 $m^2/g$ to about 1,600 $m^2/g$, about 950 $m^2/g$ to about 1,400 $m^2/g$, about 1,000 $m^2/g$ to about 1,200 $m^2/g$, or about 850 $m^2/g$ to about 1,300 $m^2/g$, for example.

The activated carbon may have an average pore diameter as small as about 0.2 nanometers (nm), about 0.5 nm, about 1 nm, about 1.5 nm, about 2 nm, or about 2.5 nm, or as large as about 3 nm, about 5 nm, about 10 nm, about 15 nm, about 20 nm, or about 25 nm, or an average pore diameter within any range defined between any two of the foregoing values, such as about 0.2 nm to about 25 nm, about 0.2 nm to about 20 nm, about 1.0 nm to about 15 nm, about 1.5 nm to about 10 nm, about 2 nm to about 5 nm, or about 2.5 nm to about 3 nm, for example.

Alternatively, the second catalyst may consist of surfaces of the second reactor itself in contact with the purified intermediate product stream, that is, an otherwise empty reactor. The surfaces may provide a catalytic effect without the need for an additional solid catalyst.

The purified intermediate product stream may be in contact with the second catalyst for a contact time as short as about 0.1 second, 1 second, about 2 seconds, about 3 seconds, about 5 seconds, about 8 seconds, about 10 seconds, about 12 seconds, or about 15 seconds, or as long as about 18 seconds, 20 seconds, about 25 seconds, about 30 seconds, about 35 seconds, about 40 seconds, about 50 seconds, about 60 seconds, or about 300 seconds, or for any contact time within any range defined between any two of the foregoing values, such as about 0.1 seconds to about 300 seconds, about 1 second to about 60 seconds, about 3 seconds to about 50 seconds, about 5 seconds to about 40 seconds, about 8 seconds to about 35 seconds, about 10 seconds to about 30 seconds, about 12 seconds to about 25 seconds, about 15 seconds to about 20 seconds, about 20 seconds to about 25 seconds, about 10 seconds to about 40 seconds, or about 10 seconds to about 30 seconds, for example. Preferably, the purified intermediate product stream may be in contact with the second catalyst for a contact time from about 1 seconds to about 60 seconds. More preferably, the purified intermediate product stream may be in contact with the second catalyst for a contact time from about 2 seconds to about 50 seconds. Most preferably, the purified intermediate product stream may be in contact with the second catalyst for a contact time from about 3 seconds to about 30 seconds.

The reaction may be maintained at a second reaction operating pressure as low as about atmospheric pressure, about 5 psig (34 kPaG), about 10 psig (69 kPaG), about 15 psig (103 kPaG), about 20 psig (138 kPaG), about 25 psig (172 kPaG), about 30 psig (207 kPaG), about 35 psig (241 kPaG), about 40 psig (276 kPaG) or about 50 psig (345 kPaG), or as high as about 60 psig (414 kPaG), about 70 psig (483 kPaG), about 80 psig (552 kPaG), about 100 psig (689 kPaG), about 120 psig (827 kPaG), about 150 psig (1,034 kPaG), about 200 psig (1,379 kPaG), about 250 psig (1,724 kPaG), or about 300 psig (2,068 KPaG), or within any range defined between any two of the foregoing values, such as about atmospheric pressure to about 300 psig (2,068 KPaG), about 5 psig (34 kPaG) to about 300 psig (2,068 kPaG), about 5 psig (34 kPaG) to about 250 psig (1,724 kPaG), about 10 psig (69 kPaG) to about 200 psig (1,379 kPaG), about 15 psig (103 kPaG) to about 150 psig (1,034 kPaG), about 20 psig (138 kPaG) to about 120 psig (827 kPaG), about 25 psig (172 kPaG) to about 100 psig (689 kPaG), about 30 psig (207 kPaG) to about 80 psig (552 kPaG), about 35 psig (241 kPaG) to about 70 psig (483 kPaG), about 40 psig (276 kPaG) to about 70 psig (483 kPaG), about 50 psig (345 kPaG) to about 60 psig (414 kPaG), 50 psig (345 kPaG) to about 250 psig (1,724 kPaG), about 100 psig (689 kPaG) to about 200 psig (1,379 kPaG), or about 150 psig (1,034 kPaG) to about 200 psig (1,379 kPaG), for example.

It has been found that the conversion rate of the trifluoroacetyl iodide may be significantly improved by operating at pressures greater than atmospheric pressure, even without the presence of the second catalyst.

The final product stream may proceed directly to a second distillation column. Alternatively, the final product stream may pass through a heat exchanger to cool the final product stream before the final product stream is provided to the second distillation column.

The final product stream comprises a composition compromising trifluoroiodomethane and carbon monoxide byproduct and unreacted trifluoroacetyl iodide, as shown in Equation 2. The final product stream composition may further include residual impurities from the purified intermediate product stream, such as trifluoroacetyl chloride ($CF_3COCl$), and chlorotrifluoroethane ($C_2H_2ClF_3$), as well as byproducts, such as trifluoromethane ($CHF_3$), hexafluoroethane ($C_2F_6$), trifluoroacetyl fluoride ($CF_3COF$), hexafluoropropanone ($CF_3COCF_3$), trifluoroacetaldehyde ($CF_3COH$), trifluorochloromethane ($CF_3Cl$), pentafluoroiodoethane ($C_2F_5I$), difluoroiodomethane ($CHF_2I$), pentafluoropropanone ($CF_3COCHF_2$), trifluoroacetic acid anhydride ($CF_3COOCOCF_3$), heptafluoroiodopropane ($C_3F_7I$), iodomethane ($CH_3I$), difluorochloroiodomethane ($CClF_2I$), and/or trifluoroacetic acid ($CF_3COOH$).

The second distillation column is configured for the separation of unreacted trifluoroacetyl iodide and by-products, such as carbon monoxide, trifluoromethane and hexafluoroethane, from the final product stream composition. The second distillation column may be configured to separate and return the unreacted trifluoroacetyl iodide to the purified intermediate product stream. The second distillation column may also be configured to separate the carbon monoxide into a carbon monoxide stream for sale, reuse elsewhere, or disposal.

In addition to the trifluoroiodomethane, the final product stream composition comprises chlorotrifluoroethane, and may also include residual carbon monoxide and hydrogen halide. The third distillation column is configured for the separation of some of the chlorotrifluoroethane from the trifluoroiodomethane. The third distillation column may also be configured for the separation of residual carbon monoxide and hydrogen chloride from the trifluoroiodomethane to produce a purified final product composition. The second distillation column and the third distillation column may include a series of distillation columns configured to additionally remove such byproducts as trifluorochloromethane, pentafluoroiodoethane, difluoroiodomethane, pentafluoropropanone, trifluoroacetic acid anhydride, heptafluoroiodopropane, iodomethane, difluorochloroiodomethane, and/or trifluoroacetic acid, as well as some of trifluoroacetyl fluoride, hexafluoropropanone, trifluoroacetaldehyde, and trifluoroacetyl chloride. The purified final product composition may be directed to a storage tank.

The purified final product composition has a trifluoroiodomethane concentration greater than 99 wt. %. Preferably, the concentration of the trifluoroiodomethane in the purified final product composition may be greater than 99.5 wt. %. More preferably, the concentration of the trifluoroiodomethane in the purified final product composition may be greater than 99.7 wt. %. Most preferably, the concentration of trifluoroiodomethane in the purified final product composition may be greater than 99.9 wt. %.

The concentration of some impurities in the purified final product stream may detract from the performance of the trifluoroiodomethane and its intended purpose as an environmentally safe, non-toxic gas. If the trifluoroacetyl halide in the reactant stream includes trifluoroacetyl chloride, the purified final product composition includes from 1 ppm (part per million by weight) to 500 ppm of chlorotrifluoroethane, less than 500 ppm hexafluoroethane, less than 500 ppm trifluoromethane, less than 100 ppm carbon monoxide, and less than 1 ppm hydrogen chloride. It is preferred that the purified final product stream includes from 1 ppm to 250 ppm of chlorotrifluoroethane, less than 250 ppm hexafluoroethane, less than 250 ppm trifluoromethane, less than 50 ppm carbon monoxide, and less than 0.5 ppm hydrogen chloride. It is more preferred that the purified final product stream includes from 1 ppm to 100 ppm of chlorotrifluoroethane, less than 10 ppm hexafluoroethane, less than 100 ppm trifluoromethane, less than 10 ppm carbon monoxide, and less than 0.2 ppm hydrogen chloride.

The purified final product composition may further comprise in amounts from 1 ppm to 500 ppm in total of compounds selected from the group consisting of trifluoroacetyl fluoride, hexafluoropropanone, trifluoroacetaldehyde, and trifluoroacetyl chloride. It is preferred that the purified final product composition further comprises in amounts from 1 ppm to 250 ppm in total of compounds selected from the group consisting of trifluoroacetyl fluoride, hexafluoropropanone, trifluoroacetaldehyde, and trifluoroacetyl chloride. It is more preferred that the purified final product composition further comprises in amounts from 1 ppm to 100 ppm in total of compounds selected from the group consisting of trifluoroacetyl fluoride, hexafluoropropanone, trifluoroacetaldehyde, and trifluoroacetyl chloride.

Alternatively stated, if the trifluoroacetyl halide in the reactant stream includes trifluoroacetyl chloride, the purified final product composition may comprise at least 99 wt. % of trifluoroiodomethane, from 1 ppm to 500 ppm chlorotrifluoroethane, less than 500 ppm hexafluoroethane, less than 500 ppm trifluoromethane, less than 100 ppm carbon monoxide, less than 1 ppm hydrogen chloride and from 1 ppm to 500 ppm in total of compounds selected from the group consisting of trifluoroacetyl fluoride, hexafluoropropanone, trifluoroacetaldehyde, and trifluoroacetyl chloride. It is also provided that the purified final product composition may comprise at least 99.5 wt. % of trifluoroiodomethane, from 1 ppm to 250 ppm chlorotrifluoroethane, less than 250 ppm hexafluoroethane, less than 250 ppm trifluoromethane, less than 50 ppm carbon monoxide, less than 0.5 ppm hydrogen chloride and from 1 ppm to 250 ppm in total of compounds selected from the group consisting of trifluoroacetyl fluoride, hexafluoropropanone, trifluoroacetaldehyde, and trifluoroacetyl chloride. It is also provided that the purified final product composition may comprise at least 99.7 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and from 1 ppm to 100 ppm in total of compounds selected from the group consisting of trifluoroacetyl fluoride, hexafluoropropanone, trifluoroacetaldehyde, and trifluoroacetyl chloride. It is also provided that the purified final product composition may comprise at least 99.9 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and from 1 ppm to 100 ppm in total of compounds selected from the group consisting of trifluoroacetyl fluoride, hexafluoropropanone, trifluoroacetaldehyde, and trifluoroacetyl chloride.

Alternatively stated, if the trifluoroacetyl halide in the reactant stream includes trifluoroacetyl chloride, the purified final product composition may consist essentially of at least 99 wt. % of trifluoroiodomethane, from 1 ppm to 500 ppm chlorotrifluoroethane, less than 500 ppm hexafluoroethane, less than 500 ppm trifluoromethane, less than 100 ppm carbon monoxide, less than 1 ppm hydrogen chloride and the balance of compounds selected from the group consisting of trifluoroacetyl fluoride, hexafluoropropanone, trifluoroacetaldehyde, and trifluoroacetyl chloride. It is also provided that the purified final product composition may consist essentially of at least 99.5 wt. % of trifluoroiodomethane, from 1 ppm to 250 ppm chlorotrifluoroethane, less than 250 ppm hexafluoroethane, less than 250 ppm trifluoromethane, less than 50 ppm carbon monoxide, less than 0.5 ppm hydrogen chloride and the balance of compounds selected from the group consisting of trifluoroacetyl fluoride, hexafluoropropanone, trifluoroacetaldehyde, and trifluoroacetyl chloride. It is also provided that the purified final product composition may consist essentially of at least 99.7 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and the balance of compounds selected from the group consisting of trifluoroacetyl fluoride, hexafluoropropanone, trifluoroacetaldehyde, and trifluoroacetyl chloride. It is also provided that the purified final product composition may consist essentially of at least 99.9 wt. % of trifluoroiodomethane, from 1 ppm to 100 ppm chlorotrifluoroethane, less than 100 ppm hexafluoroethane, less than 100 ppm trifluoromethane, less than 100 ppm carbon monoxide, less than 0.2 ppm hydrogen chloride and the balance of compounds selected from the group consisting of trifluoroacetyl fluoride, hexafluoropropanone, trifluoroacetaldehyde, and trifluoroacetyl chloride.

Alternatively stated, if the trifluoroacetyl halide in the reactant stream includes trifluoroacetyl chloride, the purified final product composition may consist of at least 99 wt. % of trifluoroiodomethane, from 1 ppm to 500 ppm chlorotrifluoroethane, less than 500 ppm hexafluoroethane, less than 500 ppm trifluoromethane, less than 100 ppm carbon monoxide, less than 1 ppm hydrogen chloride and the balance of compounds selected from the group consisting of trifluoroacetyl fluoride, hexafluoropropanone, trifluoroacetaldehyde, and trifluoroacetyl chloride. It is also provided that the purified final product composition may consist of at least 99.5 wt. % of trifluoroiodomethane, from 1 ppm to 250 ppm chlorotrifluoroethane, less than 250 ppm hexafluoroethane, less than 250 ppm trifluoromethane, less than 50 ppm carbon monoxide, less than 0.5 ppm hydrogen chloride and the balance of compounds selected from the group consisting of trifluoroacetyl fluoride, hexafluoropropanone, trifluoroacetaldehyde, and trifluoroacetyl chloride. It is also provided that the purified final product composition may consist of at least 99.7 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and the balance of compounds selected from the group consisting of trifluoroacetyl fluoride, hexafluoropropanone, trifluoroacetaldehyde, and trifluoroacetyl chloride. It is also provided that the purified final product composition may consist of at least 99.9 wt. % of trifluoroiodomethane, from 1 ppm to 100 ppm chlorotrifluoroethane, less than 100 ppm hexafluoroethane, less than 100 ppm trifluoromethane, less than 100 ppm carbon monoxide, less than 0.2 ppm hydrogen chloride and the balance of compounds selected from the group consisting of trifluoroacetyl fluoride, hexafluoropropanone, trifluoroacetaldehyde, and trifluoroacetyl chloride.

It has been found that the purified final product stream of the two-step gas-phase process described above results in a high-purity trifluoroiodomethane product due to the high purity of the trifluoroacetyl iodide in the purified intermediate product stream. The two-step gas-phase process produces surprisingly good process yields and is amenable for the manufacture of trifluoroiodomethane on a commercial scale.

Alternatively, or additionally, a reactant stream including trifluoroacetyl iodide may be provided to the second reactor for conversion into trifluoroiodomethane as described above. The reactant stream including trifluoroacetyl iodide may be produced by processes other than those described above.

FIG. 1 is a process flow diagram showing a gas-phase process 10 for manufacturing trifluoroacetyl iodide. As shown in FIG. 1, the process 10 comprises material flows of hydrogen iodide (HI) 12 and at least one trifluoroacetyl halide, trifluoroacetyl chloride ($CF_3COCl$) 14. Although trifluoroacetyl chloride is the trifluoroacetyl halide used to illustrate the processes of FIGS. 1-3, it is understood that the trifluoroacetyl halide may alternatively, or additionally, be trifluoroacetyl bromide or trifluoroacetyl fluoride. The flow of hydrogen iodide 12 and the flow of trifluoroacetyl chloride 14 are combined in a mixer valve 16 to form a reactant stream 18. The reactant stream 18 may be provided directly to a reactor 20. Alternatively, the reactant stream 18 may pass through a preheater 22 to heat the reactant stream 18 before the reactant stream 18 is provided to the reactor 20.

The trifluoroacetyl chloride and the hydrogen iodide in the reactant stream 18 react in the presence of a catalyst 24 contained within the reactor 20 to produce a product stream 26 comprising trifluoroacetyl iodide ($CF_3COI$) and hydrogen chloride (HCl) by-product according to Equation 1 above.

In addition to trifluoroacetyl iodide and hydrogen chloride, the product stream 26 further comprises unreacted trifluoroacetyl chloride and hydrogen iodide. The product stream 26 may even further comprise small amounts of other organic compounds, such as trifluoroiodomethane ($CF_3I$).

The product stream 26 may proceed directly to a distillation column 28. Alternatively, the product stream 26 may pass through a heat exchanger 30 before the product stream 26 is provided to the distillation column 28, as shown in FIG. 1. The heat exchanger 30 is configured to cool the product stream 26 before it enters the distillation column 28.

The distillation column 28 is configured for the separation of some of the by-products, reactants, and organic compounds described above from the trifluoroacetyl iodide to produce a purified product stream 32. As shown in FIG. 1, the distillation column 28 is configured to separate and return the unreacted hydrogen iodide to the flow of hydrogen iodide 12 for use in the reactant stream 18 in a hydrogen iodide flow 36 and to separate and return the unreacted trifluoroacetyl chloride to the flow of trifluoroacetyl chloride 14 for use in the reactant stream 18 in a trifluoroacetyl chloride flow 34.

The distillation column 28 is also configured to separate the hydrogen chloride into a hydrogen chloride waste stream 38 for sale, reuse elsewhere, or disposal. The purified product stream 32 comprising the trifluoroacetyl iodide is directed to a storage tank 40.

It has been found that reacting hydrogen iodide and trifluoroacetyl chloride in the presence of the catalyst 24 at the temperatures described above produces high conversion rates of the hydrogen iodide and trifluoroacetyl chloride with a high selectivity in favor of trifluoroacetyl iodide. The gas-phase process described above in reference to Equation 1 produces surprisingly good process yields and is amenable for the production of trifluoroacetyl iodide on a commercial scale.

Figure 2:
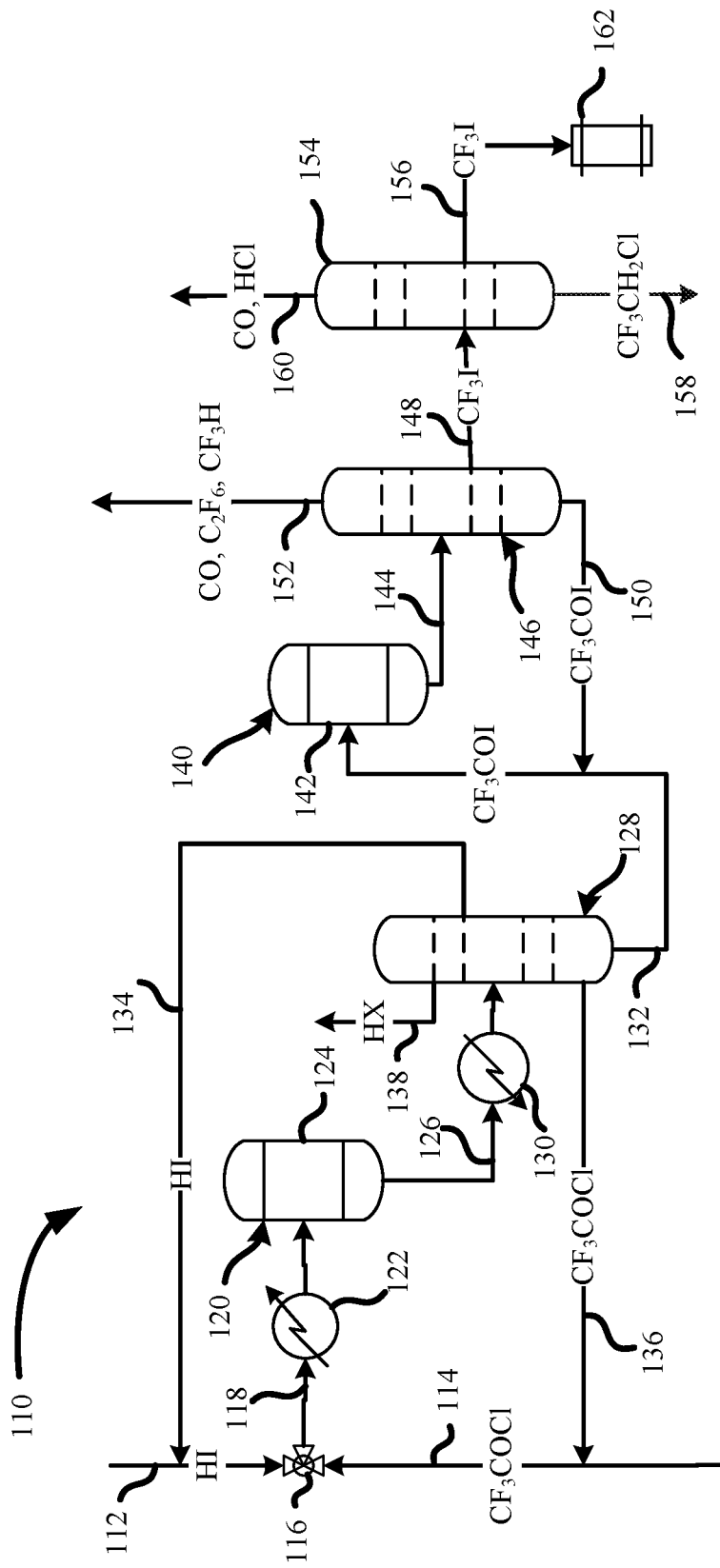
FIG. 2 is process flow diagram showing a two-step gas-phase process for manufacturing trifluoroiodomethane.

FIG. 2 is a process flow diagram showing two-step gas-phase process 110 for manufacturing trifluoroiodomethane. As shown in FIG. 2, the process 110 comprises material flows of hydrogen iodide (HI) 112 and at least one trifluoroacetyl chloride ($CF_3COCl$) 114. The flow of hydrogen iodide 112 and the flow of trifluoroacetyl chloride 114 are combined in a mixer valve 116 to form a reactant stream 118. The reactant stream 118 may be provided directly to a first reactor 120. Alternatively, the reactant stream 118 may pass through a preheater 122 to heat the reactant stream 118 before the reactant stream 118 is provided to the first reactor 120.

The trifluoroacetyl chloride and the hydrogen iodide in the reactant stream 118 react in the presence of a first catalyst 124 contained within the first reactor 120 to produce an intermediate product stream 126 comprising trifluoroacetyl iodide ($CF_3COI$) and hydrogen chloride (HCl) by-product according to Equation 1 above.

In addition to trifluoroacetyl iodide and hydrogen chloride, the intermediate product stream 126 further comprises unreacted trifluoroacetyl chloride and hydrogen iodide. The intermediate product stream 126 may even further comprise small amounts of other organic compounds, such as trifluoroiodomethane ($CF_3I$), for example.

The intermediate product stream 126 may proceed directly to a first distillation column 128. Alternatively, the intermediate product stream 126 may pass through a heat exchanger 130 before the intermediate product stream 126 is provided to the first distillation column 128, as shown in FIG. 2. The heat exchanger 130 is configured to cool the intermediate product stream 126 before it enters the first distillation column 128.

The first distillation column 128 may be configured for the separation of some of the by-products, reactants, and organic compounds described above from the trifluoroacetyl iodide to produce a purified intermediate product stream 132. As shown in FIG. 2, the first distillation column 128 is configured to separate and return the unreacted hydrogen iodide to the flow of hydrogen iodide 112 for use in the reactant stream 118 in a hydrogen iodide flow 134.

The first distillation column 128 is configured to separate and return the unreacted trifluoroacetyl chloride to the flow of trifluoroacetyl chloride 114 for use in the reactant stream 118 in a trifluoroacetyl chloride flow 136. The first distillation column 128 is also configured to separate the hydrogen chloride into a hydrogen chloride stream 138 for sale, reuse elsewhere, or disposal.

The purified intermediate product stream 132 may be provided directly to a second reactor 140, as shown in FIG. 2. Alternatively, the purified intermediate product stream 132 may pass through a preheater (not shown) to heat the purified intermediate product stream 132 before the purified intermediate product stream 132 is provided to the second reactor 140.

The trifluoroacetyl iodide in the purified intermediate product stream 132 reacts in the presence of a second catalyst 142 contained within the second reactor 140 to produce a product stream 144 comprising trifluoroiodomethane and reaction by-product carbon monoxide (CO) according to Equation 2 above.

The product stream 144 may proceed directly to a second distillation column 146, as shown in FIG. 2. Alternatively, the product stream 144 may pass through a heat exchanger (not shown) before the product stream 144 is provided to the second distillation column 146. The heat exchanger is configured to cool the product stream 144 before it enters the second distillation column 146

In addition to the trifluoroiodomethane and carbon monoxide, the product stream 144 comprises unreacted trifluoroacetyl iodide and other by-products, such as trifluoromethane ($CHF_3$), hexafluoroethane ($C_2F_6$), and chlorotrifluoroethane ($C_2H_2ClF_3$). The second distillation column 146 is configured for the separation of unreacted trifluoroacetyl iodide and by-products, such as carbon monoxide, trifluoromethane and hexafluoroethane, from the trifluoroiodomethane to produce a purified product stream 148, comprising trifluoroiodomethane. As shown in FIG. 2, the second distillation column 146 may be configured to separate and return the unreacted trifluoroacetyl iodide to the purified intermediate product stream 132 in an unreacted trifluoroacetyl iodide flow 150. The second distillation column 146 may also be configured to separate the carbon monoxide into a carbon monoxide stream 152 for sale, reuse elsewhere, or disposal.

As shown in FIG. 2, the purified product stream 148 comprising the trifluoroiodomethane is directed to a third distillation column 154 for additional purification. In addition to the trifluoroiodomethane, the purified product stream 148 includes chlorotrifluoroethane, and may also include residual carbon monoxide and hydrogen chloride. The third distillation column 154 is configured for the separation of the chlorotrifluoroethane from the trifluoroiodomethane to produce a purified final product stream 156 comprising trifluoroiodomethane. As shown in FIG. 2, the third distillation column 154 may be configured to separate the chlorotrifluoroethane into a chlorotrifluoroethane stream 158 for sale, reuse elsewhere, or disposal. The third distillation column 154 may also be configured to separate the carbon monoxide and hydrogen chloride into a waste stream 160 for disposal. The purified final product stream 156 comprising the trifluoroiodomethane may be directed to a storage tank 162.

Figure 3:
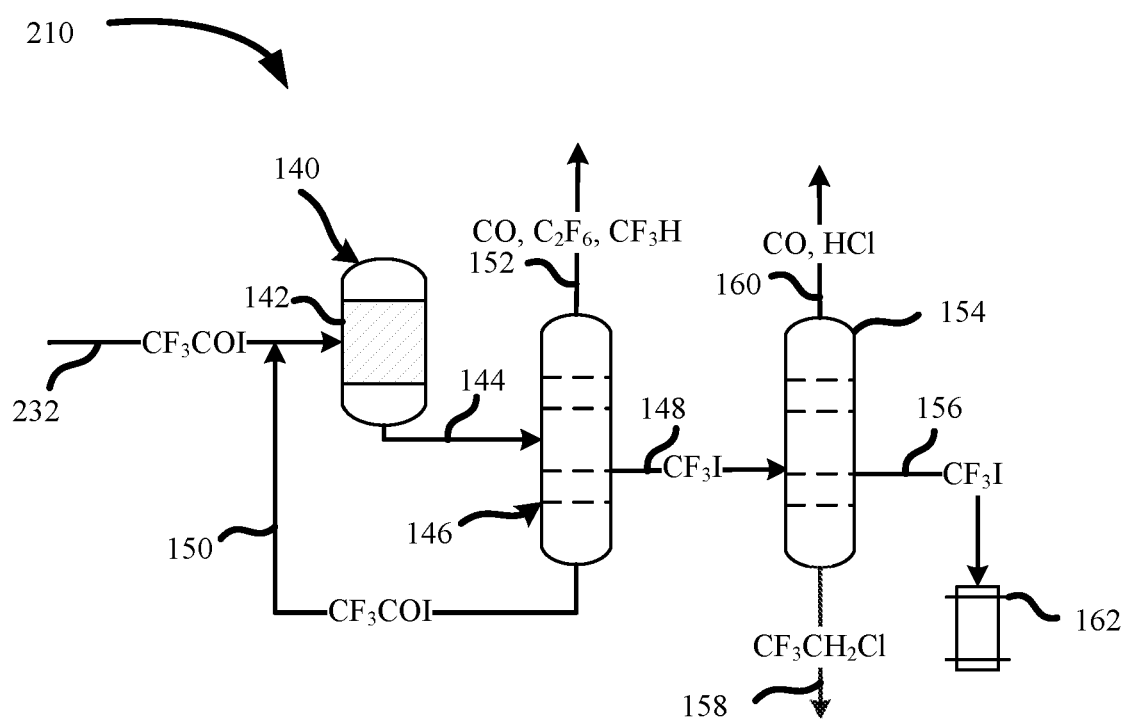
FIG. 3 is a process flow diagram showing a gas-phase process for manufacturing trifluoroiodomethane from trifluoroacetyl iodide.

FIG. 3 is a process flow diagram showing a process 210 for manufacturing trifluoroiodomethane from trifluoroacetyl iodide. The process 210 may be identical to the second step of the two-step process described above and in reference to FIG. 2, except that the purified intermediate product stream 132 is replaced by a reactant stream 232. The reactant stream 232 includes trifluoroacetyl iodide. The trifluoroacetyl iodide may be produced by processes other than those described herein. The reactant stream 232 may further include trifluoroacetyl iodide produced by processes described herein.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Example 1: Manufacture of Trifluoroacetyl Iodide According to Equation 1 at Higher Reaction Temperatures In this Example, the manufacture of trifluoroacetyl iodide from hydrogen iodide and trifluoroacetyl chloride according to Equation 1 at higher temperatures as described above is demonstrated. Equimolar amounts of trifluoroacetyl chloride and anhydrous hydrogen iodide were passed through a preheater and heated to a temperature of about 100° C. in a series of twenty-three experiments. The heated reactants were passed through a stainless-steel tube ⅜ inch (9.5 mm) in diameter and 6 inches (152 mm) in length. The tube was heated to temperatures ranging from 200° C. to 350° C., depending on the experiment, and purged with nitrogen for at least one hour before each experiment to drive off any water. In twenty-one experiments, the tube contained one of several catalysts. In the remaining two experiments, the tube did not contain a catalyst. Contact times were varied from 10 seconds to 30 seconds. All exiting vapors for each experiment were collected in a sample bags for GC and GC-MS analyses. The results are shown in Tables 1, 2, and 3.

Table 1 lists the reaction conditions (temperature, contact time, and catalyst used) for each of the twenty-three experiments. Table 2 lists the GC area % of the primary organic compounds of interest corresponding to each of the twenty-three experiments. Table 3 lists a conversion percentage and selectivity percentages for trifluoroiodomethane, trifluoroacetyl iodide, and the combination of trifluoroiodomethane and trifluoroacetyl iodide corresponding to each of the twenty-three experiments. Conversion and selectivity percentages are based on the GC area % data.

As shown in Tables 1, 2, and 3, the process described above in reference to Equation 1 is able to produce trifluoroacetyl iodide with conversion percentages exceeding 90% and selectivity percentages exceeding 99%. Thus, Tables 1, 2, and 3 demonstrate processes in accordance with this disclosure for the production of trifluoroacetyl iodide that produce surprisingly good results.

TABLE 1

Reaction Conditions

| Experiment Number | Temp. (° C.) | Contact Time (seconds) | Catalyst |
|---|---|---|---|
| 1 | 200 | 30 | Empty Stainless-Steel Tube |
| 2 | 350 | 20 | Empty Stainless-Steel Tube |
| 3 | 200 | 30 | ProPak ®-Stainless Steel |
| 4 | 350 | 20 | ProPak ®-Stainless Steel |
| 5 | 200 | 30 | ProPak ®-Hastelloy C |
| 6 | 350 | 20 | ProPak ®-Hastelloy C |
| 7 | 200 | 30 | Cu Mesh |
| 8 | 350 | 20 | Cu Mesh |
| 9 | 200 | 30 | Activated Carbon-Shirasagi |
| 10 | 350 | 20 | Activated Carbon-Shirasagi |
| 11 | 200 | 30 | Activated Carbon-PCP-LS 4 × 10 |
| 12 | 350 | 20 | Activated Carbon-PCP-LS 4 × 11 |
| 13 | 200 | 30 | Activated Carbon-X2M 4/6 |
| 14 | 350 | 20 | Activated Carbon-X2M 4/7 |
| 15 | 200 | 30 | Activated Carbon-Calgon Carbon |
| 16 | 350 | 20 | Activated Carbon-Calgon Carbon |
| 17 | 200 | 30 | Gamma Alumina |
| 18 | 350 | 20 | Gamma Alumina |
| 19 | 200 | 30 | Activated Carbon, Norit-PK35 |
| 20 | 250 | 28 | 0.5% Pd on alumina |
| 21 | 250 | 32 | 0.5% Pd on alumina |
| 22 | 225 | 10 | Silicon carbide |
| 23 | 200 | 10 | Silicon carbide |

TABLE 2

Products GC Area %

| Experiment Number | $CHF_3$ | $CF_3Cl$ | $CF_3COCl$ | $CF_3I$ | $CF_3COI$ | Others (sum) |
|---|---|---|---|---|---|---|
| 1 | 0.08 | | 49.12 | 0.1 | 48.61 | 2.09 |
| 2 | | | 44.27 | 0.23 | 51.95 | 3.55 |
| 3 | | | 44.25 | 0.12 | 48.63 | 7 |
| 4 | 0.02 | | 30.58 | 0.07 | 65.6 | 3.73 |
| 5 | | | 80.31 | | 17.9 | 1.79 |
| 6 | | | 78.99 | | 18.14 | 2.87 |
| 7 | 0.02 | | 72.49 | | 23.59 | 3.9 |
| 8 | 0.02 | | 58.02 | | 39.03 | 2.93 |
| 9 | 0.03 | | 94.29 | | 3.8 | 1.88 |
| 10 | 2.3 | | 58.22 | 31.37 | 6.18 | 1.93 |
| 11 | | | 91.29 | 0.18 | 6.2 | 2.33 |
| 12 | | | 35.09 | 56.12 | 3.81 | 4.98 |
| 13 | | | 82.79 | 0.05 | 15.92 | 1.24 |
| 14 | | | 64.33 | 12.81 | 20.93 | 1.93 |
| 15 | | | 80.9 | 0.2 | 14.25 | 4.65 |
| 16 | | 1.75 | 55.51 | 26.09 | 12.3 | 4.35 |
| 17 | | | 35.61 | 0.26 | 52.29 | 11.84 |
| 18 | | 5.14 | 47.28 | 1.56 | 33.91 | 12.11 |
| 19 | 0.04 | | 22.7 | 0.32 | 74.65 | 2.29 |
| 20 | | 0.03 | 5.27 | 0.12 | 93.8 | 0.78 |
| 21 | | 0.02 | 2.07 | 0.35 | 93.9 | 3.66 |
| 22 | | | 5.05 | 1.69 | 87.8 | 5.46 |
| 23 | | | 3.61 | 0.31 | 92.02 | 4.06 |

TABLE 3

Conv. % and Sel. %

| Experiment Number | Conv. % | Sel. % $CF_3I$ Only | Sel. % $CF_3COI$ Only | Sel. % $CF_3I$ + $CF_3COI$ |
|---|---|---|---|---|
| 1 | 50.9 | 0.2 | 95.5 | 95.7 |
| 2 | 55.7 | 0.4 | 93.2 | 93.6 |
| 3 | 55.8 | 0.2 | 87.2 | 87.4 |
| 4 | 69.4 | 0.1 | 94.5 | 94.6 |
| 5 | 19.7 | 0.0 | 90.9 | 90.9 |

TABLE 3-continued

| | | Conv. % and Sel. % | | |
|---|---|---|---|---|
| Experiment Number | Conv. % | Sel. % CF$_3$I Only | Sel. % CF$_3$COI Only | Sel. % CF$_3$I + CF$_3$COI |
| 6  | 21.0 | 0.0  | 86.3 | 86.3 |
| 7  | 27.5 | 0.0  | 85.8 | 85.8 |
| 8  | 42.0 | 0.0  | 93.0 | 93.0 |
| 9  | 5.7  | 0.0  | 66.5 | 66.5 |
| 10 | 41.8 | 75.1 | 14.8 | 89.9 |
| 11 | 8.7  | 2.1  | 71.2 | 73.2 |
| 12 | 64.9 | 86.5 | 5.9  | 92.3 |
| 13 | 17.2 | 0.3  | 92.5 | 92.8 |
| 14 | 35.7 | 35.9 | 58.7 | 94.6 |
| 15 | 19.1 | 1.0  | 74.6 | 75.7 |
| 16 | 44.5 | 58.6 | 27.6 | 86.3 |
| 17 | 64.4 | 0.4  | 81.2 | 81.6 |
| 18 | 52.7 | 3.0  | 64.3 | 67.3 |
| 19 | 77.3 | 0.4  | 96.6 | 97.0 |
| 20 | 94.7 | 0.1  | 99.0 | 99.1 |
| 21 | 97.9 | 0.4  | 95.9 | 96.2 |
| 22 | 95.0 | 1.8  | 92.5 | 94.2 |
| 23 | 96.4 | 0.3  | 95.5 | 95.8 |

Example 2: Manufacture of Trifluoroacetyl Iodide According to Equation 1 at a Higher Reaction Temperature In this Example, the manufacture of trifluoroacetyl iodide from hydrogen iodide and trifluoroacetyl chloride according to Equation 1 at a higher reaction temperature as described above is demonstrated. Trifluoroacetyl chloride at flow rate of 8.34 g/hour of and hydrogen iodide at a flow rate of 14.08 g/hour were passed through a stainless-steel tube ⅜ inch (9.5 mm) in diameter and 6 inches (152 mm) in length. The tube was heated to about 300° C., and purged with nitrogen for at least one hour before the experiment to drive off any water. The tube contained a catalyst of Pro-Pak® stainless steel for a contact time of about 10 seconds. The process was run continuously for 6.25 hours. The output of the reactor was collected in two dry ice traps, one at around 0° C. to –5° C. and the other at around –78° C.

A total of 99.8 g of material was collected and a portion analyzed by GC and GC-MS. The collected material was found to contain a mixture of trifluoroacetyl iodide and trifluoroacetyl chloride in a 60:40 ratio. The selectivity of trifluoroacetyl iodide ranged from 88% to 97% based on the GC area %.

Example 3: Manufacture of Trifluoroacetyl Iodide According to Equation 1 at a Higher Reaction Temperature In this Example, the manufacture of trifluoroacetyl iodide from hydrogen iodide and trifluoroacetyl chloride according to Equation 1 at a higher reaction temperature as described above is demonstrated. Trifluoroacetyl chloride at flow rate of 5.75 g/hour of and hydrogen iodide at a flow rate of 13.9 g/hour were passed through a stainless-steel tube ½ inch (12.7 mm) in diameter and 6 inches (152 mm) in length. The tube was heated to about 250° C., and purged with nitrogen for at least one hour before the experiment to drive off any water. The tube contained a catalyst of 0.5% palladium on an alumina support (3.2 mm pellets) for a contact time of about 15 seconds. The process was run continuously for 5.25 hours. The output of the reactor was collected in two dry ice traps, one at around 0° C. to –5° C. and the other at around –78° C.

A total of 89 g of material was collected and a portion analyzed by GC-MS. The collected material was found to contain a mixture of trifluoroacetyl iodide and trifluoroacetyl chloride in a 70:30 ratio. Selectivity of trifluoroacetyl iodide to trifluoroiodomethane ranged from 92% to 98% based on the GC area %. This example was repeated with a catalyst of silicon carbide (3 mm pellets) with similar results Example 4: Manufacture of Trifluoroacetyl Iodide According to Equation 1 at Lower Reaction Temperatures In this Example, the manufacture of trifluoroacetyl iodide from hydrogen iodide and trifluoroacetyl chloride according to Equation 1 at lower temperatures as described above is demonstrated. Amounts of trifluoroacetyl chloride and anhydrous hydrogen iodide in specific molar ratios were passed through a metal tube ¾ inch (19.05 mm) in diameter. A pressure transducer and control valve at the outlet of the reactor were used to control the pressure. The tube was heated to temperatures ranging from 40° C. to 210° C., depending on the experiment. In twenty-six of the twenty-eight experiments, the tube contained one of several catalysts. In the remaining two experiments, the tube did not contain a catalyst. Contact times were varied from 6.1 seconds to 71.7 seconds. The reactor effluent for each experiment passed through a heat-traced line to prevent condensation of the trifluoroacetyl iodide and directed to a dry-ice trap to capture the crude product. Uncondensed vapors escaping from the dry-ice trap were directed to a water scrubber and a caustic scrubber. Samples were taken from the reactor effluent for GC and GC-MS analyses. A contact time in the reactor was calculated for each experiment based on the combined feed rates of the trifluoroacetyl chloride and the hydrogen iodide. Run times ranged from 8 hours to 49 hours. At the end of run time for the reaction for each experiment, the system was shut down and all containers were weighted to for mass balance purposes. The crude product collected in the dry-ice trap was also sampled and analyzed for GC and GC-MS analysis. The results are shown in Tables 4 and 5.

Table 4 lists the reaction conditions (temperature, mole ratio, contact time, reactor type, pressure and catalyst used) for each of the twenty-eight experiments. Table 5 lists the GC area % of the primary organic compounds of interest as well as a conversion percentage of the trifluoroacetyl chloride and selectivity to trifluoroacetyl iodide corresponding to each of the twenty-eight experiments. Conversion and selectivity percentages are based on the GC area % data.

As shown in Tables 4 and 5, the process described above in reference to Equation 1 operating at reaction temperatures at or below about 120° C. is able to produce trifluoroacetyl iodide with a concentration of trifluoroiodomethane less than 0.002%, or about 20 ppm, of the total organic compounds with conversion percentages exceeding 80% (with a catalyst and with trifluoroacetyl chloride to hydrogen ratios around unity) and selectivity for trifluoroacetyl iodide of 99 mol % or greater. Thus, Tables 4 and 5 demonstrate processes in accordance with this disclosure for the production of trifluoroacetyl iodide that produce surprisingly good results.

TABLE 4

| Exp. No. | Temp. (° C.) | CF₃COCl:HI (mole ratio) | Contact Time (seconds) | Reactor Tube (Inconel Type) | Pressure | Catalyst |
|---|---|---|---|---|---|---|
| 1 | 210 | 0.99 | 21 | 600 | 0 psig/kPaG | None |
| 2 | 210 | 1.43 | 6.1 | 600 | 0 psig/kPaG | 0.5% Pd/Al₂O₃ |
| 3 | 210 | 1.12 | 6.8 | 600 | 0 psig/kPaG | Silicon Carbide (SiC2-E3-HP) |
| 4 | 210 | 0.95 | 6.3 | 600 | 0 psig/kPaG | Silicon Carbide (SiC2-E3-HP) |
| 5 | 180 | 0.99 | 7.8 | 600 | 0 psig/kPaG | Silicon Carbide (SiC2-E3-HP) |
| 6 | 150 | 0.99 | 8.4 | 600 | 0 psig/kPaG | Silicon Carbide (SiC2-E3-HP) |
| 7 | 120 | 0.99 | 9.0 | 600 | 0 psig/kPaG | Silicon Carbide (SiC2-E3-HP) |
| 8 | 90 | 0.96 | 8.6 | 600 | 0 psig/kPaG | Silicon Carbide (SiC2-E3-HP) |
| 9 | 60 | 0.96 | 9.4 | 600 | 0 psig/kPaG | Silicon Carbide (SiC2-E3-HP) |
| 10 | 40 | 0.99 | 10.2 | 600 | 0 psig/kPaG | Silicon Carbide (SiC2-E3-HP) |
| 11 | 60 | 0.99 | 12.9 | 600 | 5 psig (34.5 kPaG) | Silicon Carbide (SiC2-E3-HP) |
| 12 | 60 | 0.99 | 19.4 | 600 | 15 psig (103 kPaG) | Silicon Carbide (SiC2-E3-HP) |
| 13 | 60 | 0.92 | 18.5 | 600 | 15 psig (103 kPaG) | Activated Carbon (Norit ROX0.8) |
| 14 | 90 | 0.92 | 17.0 | 600 | 15 psig (103 kPaG) | Activated Carbon (Norit ROX0.8) |
| 15 | 120 | 0.92 | 15.7 | 600 | 15 psig (103 kPaG) | Activated Carbon (Norit ROX0.8) |
| 16 | 40 | 0.92 | 19.7 | 600 | 15 psig (103 kPaG) | Activated Carbon (Norit ROX0.8) |
| 17 | 60 | 0.79 | 18.0 | 600 | 15 psig (103 kPaG) | Activated Carbon (CPG CF12X40) |
| 18 | 90 | 0.79 | 16.5 | 600 | 15 psig (103 kPaG) | Activated Carbon (CPG CF12X40) |
| 19 | 60 | 0.80 | 16.5 | 600 | 15 psig (103 kPaG) | Activated Carbon (OLC12X30) |
| 20 | 90 | 0.80 | 15.1 | 600 | 15 psig (103 kPaG) | Activated Carbon (OLC12X30) |
| 21 | 60 | 0.79 | 17.1 | 600 | 15 psig (103 kPaG) | Activated Carbon (JEChem C2X8/12) |
| 22 | 90 | 0.79 | 15.7 | 600 | 15 psig (103 kPaG) | Activated Carbon (JEChem C2X8/12) |
| 23 | 90 | 0.75 | 15.6 | 600 | 15 psig (103 kPaG) | Activated Carbon (Norit ROX0.8) |
| 24 | 90 | 1.40 | 20.1 | 600 | 15 psig (103 kPaG) | Activated Carbon (Norit ROX0.8) |
| 25 | 90 | 1.56 | 71.7 | 625 | 15 psig (103 kPaG) | None |
| 26 | 90 | 1.43 | 22.3 | 625 | 20 psig (138 kPaG) | Inconel 625 Wire Mesh |
| 27 | 90 | 1.38 | 27.1 | 600 | 20 psig (138 kPaG) | Silicon Carbide (SiC1-E3-P) |
| 28 | 90 | 1.27 | 24.5 | 600 | 20 psig (138 kPaG) | Silicon Carbide (SiC1-E3-HP) |

TABLE 5

| Exp. No. | CF$_3$COCl (GC area %) | CF$_3$I (GC area %) | C$_2$H$_2$ClF$_3$ (GC area %) | CF$_3$COI (GC area %) | Others (GC area %) | Conversion of CF$_3$COCl (mol %) | Selectivity of CF$_3$COI (mol %) |
|---|---|---|---|---|---|---|---|
| 1 | 56.22 | 0.002 | 0.037 | 38.90 | 4.84 | 43.46 | |
| 2 | 21.45 | 0.43 | 0.024 | 73.79 | 4.31 | 78.01 | |
| 3 | 18.89 | 2.91 | 0.012 | 76.41 | 1.78 | 81.90 | |
| 4 | 18.03 | 3.22 | 0.017 | 75.73 | 3.00 | 81.38 | |
| 5 | 17.11 | 0.25 | 0.022 | 79.99 | 2.63 | 82.77 | |
| 6 | 17.44 | 0.012 | 0.027 | 80.71 | 1.81 | 82.49 | |
| 7 | 16.56 | 0 | 0.037 | 81.63 | 1.77 | 83.37 | |
| 8 | 11.27 | 0 | 0.026 | 83.13 | 5.57 | 88.30 | |
| 9 | 12.35 | 0 | 0.027 | 83.70 | 3.92 | 87.59 | |
| 10 | 12.81 | 0 | 0.027 | 82.80 | 4.36 | 87.12 | |
| 11 | 14.05 | 0 | 0.029 | 83.26 | 2.66 | 85.89 | |
| 12 | 14.27 | 0 | 0.030 | 83.51 | 2.19 | 85.69 | |
| 13 | 14.59 | 0 | 0.031 | 83.57 | 1.81 | 85.34 | |
| 14 | 12.55 | 0 | 0.029 | 85.86 | 1.56 | 87.38 | |
| 15 | 14.50 | 0.0014 | 0.032 | 82.36 | 3.11 | 85.22 | |
| 16 | 20.85 | 0 | 0.035 | 75.94 | 3.18 | 79.08 | |
| 17 | 9.01 | 0 | 0.031 | 87.22 | 3.74 | 90.82 | |
| 18 | 10.45 | 0 | 0.033 | 86.09 | 3.43 | 89.46 | |
| 19 | 9.60 | 0 | 0.032 | 86.04 | 4.33 | 90.28 | |
| 20 | 11.21 | 0 | 0.035 | 85.09 | 3.67 | 88.70 | |
| 21 | 11.06 | 0 | 0.036 | 85.31 | 3.59 | 88.86 | |
| 22 | 10.62 | 0 | 0.036 | 86.16 | 3.18 | 89.31 | |
| 23 | 11.48 | 0 | 0.038 | 86.10 | 2.38 | 88.43 | |
| 24 | 28.50 | 0 | 0.40 | 69.93 | 1.17 | 71.38 | |
| 25 | 62.36 | 0 | 0.069 | 35.30 | 2.27 | 37.56 | |
| 26 | 66.36 | 0 | 0.072 | 30.82 | 2.75 | 33.54 | 99.99 |
| 27 | 31.57 | 0 | 0.047 | 65.66 | 2.72 | 68.28 | 99.97 |
| 28 | 21.72 | 0 | 0.050 | 76.03 | 2.20 | 78.09 | 99.03 |

Example 5: Evaluation of SiC Catalyst Lifetime in the Manufacture of Trifluoroacetyl Iodide According to Equation 1 at a Lower Reaction Temperature In this Example, the lifetime of a silicon carbide catalyst (SiC1-E3-M) was evaluated in the manufacture of trifluoroacetyl iodide from hydrogen iodide and trifluoroacetyl chloride according to Equation 1 at 90° C. In this Example, 20 mL of the silicon carbide catalyst was loaded into an Inconel 600 tube ¾ inch (19.05 mm) in diameter. A pressure transducer and control valve at the outlet of the reactor were used to control the pressure to 20 psig (138 kPaG). Periodically, the system was shut down to check the mass balance and collect the crude product for analysis. This was repeated for a series of five runs extending over a total run time of over 455 hours. The results are shown in Table 6.

Table 6 lists the reaction conditions (mole ratio, contact time, time on stream and cumulative time on stream) for each of the five consecutive runs. Table 6 also lists a conversion percentage of the trifluoroacetyl chloride, selectivity to trifluoroacetyl iodide and the GC area % of trifluoroiodomethane for each of the five consecutive runs. Conversion and selectivity percentages are based on GC area % data.

As shown in Table 6, the process described above in reference to Equation 1 operating at reaction temperatures at 90° C. is able to produce trifluoroacetyl iodide with no detectable trifluoroiodomethane formation. No deactivation of the silicon carbide catalyst was observed during over 455 hours of operation.

TABLE 6

| Run. No. | CF$_3$COCl:HI (mole ratio) | Contact Time (seconds) | Time On Stream (hrs) | Total Time On Stream (hrs) | Conversion of CF3COCl (mol %) | Selectivity of CF3COI (mol %) | CF3I (GC area %) |
|---|---|---|---|---|---|---|---|
| 1 | 1.14 | 23.92 | 96 | 96 | 77.92 | 99.96 | 0.00 |
| 2 | 1.25 | 24.67 | 96 | 192 | 74.99 | 99.95 | 0.00 |
| 3 | 1.32 | 24.50 | 96 | 288 | 73.53 | 99.95 | 0.00 |
| 4 | 1.24 | 25.25 | 100 | 388 | 72.24 | 99.9 | 0.00 |
| 5 | 1.32 | 25.24 | 67.25 | 455.25 | 81.75 | 99.91 | 0.00 |

Example 6: Evaluation of Activated Carbon Catalyst Lifetime in the Manufacture of Trifluoroacetyl Iodide According to Equation 1 at a Lower Reaction Temperature In this Example, the lifetime of an activated carbon catalyst (Norit ROX0.8) was evaluated in the manufacture of trifluoroacetyl iodide from hydrogen iodide and trifluoroacetyl chloride according to Equation 1 at 90° C. In this Example, 20 mL of the activated carbon catalyst was loaded into an Inconel 600 tube ¾ inch (19.05 mm) in diameter. A pressure transducer and control valve at the outlet of the reactor were used to control the pressure. Periodically, the system was shut down to check the mass balance and collect the crude product for analysis. This was repeated for a series of twenty-nine runs extending over a total run time of over 2,000 hours. The results are shown in Table 7.

Table 7 lists the reaction conditions (pressure, mole ratio, contact time, time on stream and cumulative time on stream) for each of the twenty-nine consecutive runs. Table 7 also lists a conversion percentage of the trifluoroacetyl chloride, selectivity to trifluoroacetyl iodide and the GC area % of trifluoroiodomethane for each of the twenty-nine consecutive runs. Conversion and selectivity percentages are based on GC area % data.

As shown in Table 7, the process described above in reference to Equation 1 operating at reaction temperatures at 90° C. is able to produce trifluoroacetyl iodide with no detectable trifluoroiodomethane formation. No deactivation of the activated carbon catalyst was observed during over 2,051 hours of operation.

TABLE 7

| Run. No. | Pressure | $CF_3COCl:HI$ (mole ratio) | Contact Time (seconds) | Time On Stream (hrs) | Total Time On Stream (hrs) | Conversion of CF3COCl (mol %) | Selectivity of CF3COI (mol %) | CF3I (GC area %) |
|---|---|---|---|---|---|---|---|---|
| 1 | 50 psig (345 kPaG) | 1.86 | 37.7 | 97.75 | 97.75 | 71.81 | | |
| 2 | 50 psig (345 kPaG) | 0.95 | 57.9 | 87.50 | 185.25 | 94.03 | | |
| 3 | 30 psig (207 kPaG) | 1.36 | 28.1 | 42.75 | 228.00 | 78.88 | | |
| 4 | 20 psig (138 kPaG) | 1.36 | 21.8 | 52.00 | 280.00 | 56.81 | | |
| 5 | 20 psig (138 kPaG) | 1.61 | 28.4 | 12.00 | 292.00 | 55.68 | | |
| 6 | 20 psig (138 kPaG) | 1.47 | 24.2 | 93.25 | 385.25 | 70.05 | 99.89 | 0.00 |
| 7 | 30 psig (207 kPaG) | 1.32 | 30.7 | 98.50 | 483.75 | 70.49 | 99.95 | 0.00 |
| 8 | 30 psig (207 kPaG) | 1.10 | 34.4 | 100.00 | 583.75 | 71.71 | 99.94 | 0.00 |
| 9 | 20 psig (138 kPaG) | 1.39 | 23.3 | 97.50 | 681.25 | 73.40 | 99.98 | 0.00 |
| 10 | 20 psig (138 kPaG) | 0.95 | 18.9 | 92.50 | 773.75 | 84.02 | 99.74 | 0.00 |
| 11 | 20 psig (138 kPaG) | 1.07 | 20.2 | 91.50 | 865.25 | 77.01 | 99.86 | 0.00 |
| 12 | 20 psig (138 kPaG) | 1.61 | 24.11 | 86.00 | 951.25 | 60.70 | 99.79 | 0.00 |
| 13 | 20 psig (138 kPaG) | 1.34 | 22.53 | 46.00 | 997.25 | 70.84 | 99.76 | 0.00 |
| 14 | 20 psig (138 kPaG) | 1.95 | 24.50 | 6.50 | 1003.75 | 56.18 | 97.28 | 0.00 |
| 15 | 20 psig (138 kPaG) | 1.40 | 22.94 | 58.00 | 1061.75 | 66.98 | 99.69 | 0.00 |
| 16 | 20 psig (138 kPaG) | 1.55 | 23.84 | 48.50 | 1110.25 | 63.61 | 99.98 | 0.00 |
| 17 | 20 psig (138 kPaG) | 1.51 | 23.38 | 48.00 | 1158.25 | 64.21 | 99.98 | 0.00 |
| 18 | 20 psig (138 kPaG) | 1.39 | 34.14 | 48.00 | 1206.25 | 52.92 | 99.85 | 0.00 |
| 19 | 20 psig (138 kPaG) | 1.40 | 22.98 | 25.17 | 1231.42 | 64.97 | 99.98 | 0.00 |
| 20 | 20 psig (138 kPaG) | 1.29 | 22.01 | 100 | 1331.42 | 73.38 | 99.97 | 0.00 |
| 21 | 20 psig (138 kPaG) | 1.27 | 21.96 | 101.25 | 1432.67 | 67.59 | 99.94 | 0.00 |
| 22 | 20 psig (138 kPaG) | 1.51 | 24.05 | 23.00 | 1455.67 | 59.30 | 99.97 | 0.00 |

TABLE 7-continued

| Run. No. | Pressure | CF$_3$COCl:HI (mole ratio) | Contact Time (seconds) | Time On Stream (hrs) | Total Time On Stream (hrs) | Conversion of CF3COCl (mol %) | Selectivity of CF3COI (mol %) | CF3I (GC area %) |
|---|---|---|---|---|---|---|---|---|
| 23 | 20 psig (138 kPaG) | 1.45 | 23.45 | 96.00 | 1551.67 | 60.89 | 99.88 | 0.00 |
| 24 | 20 psig (138 kPaG) | 3.37 | 30.87 | 45.00 | 1596.67 | 24.23 | 99.90 | 0.00 |
| 25 | 20 psig (138 kPaG) | 1.41 | 23.14 | 96.00 | 1692.67 | 67.87 | 99.96 | 0.00 |
| 26 | 20 psig (138 kPaG) | 1.43 | 23.36 | 96.00 | 1788.67 | 68.66 | 99.98 | 0.00 |
| 27 | 20 psig (138 kPaG) | 1.19 | 21.61 | 96.00 | 1884.67 | 72.98 | 99.94 | 0.00 |
| 28 | 20 psig (138 kPaG) | 1.60 | 24.34 | 100.00 | 1984.67 | 60.64 | 99.93 | 0.00 |
| 29 | 20 psig (138 kPaG) | 1.37 | 23.00 | 67.25 | 2051.92 | 59.38 | 99.96 | 0.00 |

Example 7: Separation of Trifluoroacetyl Iodide

In this Example, the separation of trifluoroacetyl iodide is described. A mixture containing about 80 wt. % trifluoroacetyl iodide, about 10 wt. % trifluoroacetyl chloride, about 5 wt. % hydrogen iodide, and about 5 wt. % hydrogen chloride can be charged into a distillation column. The distillation column can include a 10 gallon reboiler, a 2-inch inside diameter 10-foot Pro-Pak® column from the Cannon Instrument Company, State College, Pa., and about 30 theoretical plates. The distillation column can be equipped with temperature, absolute pressure, and differential pressure transmitters. The distillation can be run at a pressure of about 300 kPaG and at a temperature of about 55° C., with hydrogen chloride taken off from the top of the column, and product from the bottom of the column.

Example 8: Manufacture of Trifluoroiodomethane from Trifluoroacetyl Iodide According to Equation 2 with an Activated Carbon Catalyst at Atmospheric Pressure In this Example, the manufacture of trifluoroiodomethane from trifluoroacetyl iodide according to Equation 2 described above at atmospheric pressure is demonstrated. A mixture of 55 GC area % trifluoroacetyl iodide and 45 GC area % trifluoroacetyl chloride was passed through a preheater and heated to a temperature of about 100° C. The heated reactants were passed through a stainless-steel tube ⅜ inch (9.5 mm) in diameter and 6 inches (152 mm) in length. The tube was heated to about 350° C., and purged with nitrogen for at least one hour before the experiment to drive off any water. The tube contained a catalyst of Norit-PK35 activated carbon for a contact time of about 10-15 seconds. The output of the reactor was collected in a sample bag for GC and GC-MS analyses.

Near complete conversion of trifluoroacetyl iodide to trifluoroiodomethane was observed. The ratio of trifluoroiodomethane to unreacted trifluoroacetyl iodide was 54:0.22 for an unreacted trifluoroacetyl iodide of less than 0.5%, based on the GC area % measurements.

Example 9: Manufacture of Trifluoroiodomethane from Trifluoroacetyl Iodide According to Equation 2 without a Catalyst at Above Atmospheric Pressure In this Example, the manufacture of trifluoroiodomethane from trifluoroacetyl iodide according to Equation 2 described above at pressures above atmospheric pressure and without a separate catalyst is demonstrated. A feed stream of at least 99.22 GC area % trifluoroacetyl iodide was passed through a heated tube. The heated tube was a commercially pure (>99%) wrought nickel tube 0.5 inch (12.7 mm) in diameter with a heated zone 120 mm in length. The flow rate through produced a contact time of about 10 seconds. The tube contained no catalyst. The feed had a contact time of about 10 seconds. A pressure transducer and control valve at the outlet of the reactor were used to control the pressure. The output of the reactor was collected in a sample bag for GC and GC-MS analyses. The results are shown in Table 8.

Table 8 lists the reaction conditions (temperature, pressure) for each of the twenty experiments. Table 8 also lists a conversion percentage of the trifluoroacetyl iodide and selectivity to trifluoroiodomethane for each of the twenty experiments. Conversion and selectivity percentages are based on GC area % data. Table 8 also lists the GC area % of the primary organic compounds of interest corresponding to some of the twenty-eight experiments Considering the results of experiments 1-10 as shown in Table 8, the process described above in reference to Equation 2 operating at higher reaction pressures is able to produce trifluoroiodomethane with both a high conversion rate of the trifluoroacetyl iodide and high selectivity to forming trifluoroiodomethane. This effect was observed without the use of a catalyst, other than any catalytic effect provided by the nickel reactor itself. While the use of a catalyst may provide improved results, particularly at lower reaction temperatures, not having to regenerate or replace a catalyst can provide for a more efficient process overall.

Considering the results of experiments 11-20 as shown in Table 8, is it shown that the improved results, without a catalyst, are particularly pronounced at higher pressures combined with higher temperatures, with improved results shown at temperatures of 300° C. or greater at an operating pressure at 200 psig (exp. 11-15) compared to operating at atmospheric pressure (exp. 16-20).

with temperature, absolute pressure, and differential pressure transmitters. The distillation can be run at a pressure of about 275 kPaG and a condenser at a temperature of about −13° C. to collect trifluoroiodomethane.

TABLE 8

| Exp. No. | Temp. (° C.) | Pressure | $CF_3I$ (GC area %) | $CF_3COI$ (GC area %) | $CF_3COCl$ (GC area %) | Others (GC area %)) | Conversion of $CF_3COI$ (%) | Selectivity of $CF_3I$ (%) |
|---|---|---|---|---|---|---|---|---|
| 1 | 350 | 0 psig (kPaG) | | | | | 63 | 98.9 |
| 2 | 350 | 50 psig (345 kPaG) | 67.99 | 31.62 | 0.17 | 0.22 | 68.3 | 99.4 |
| 3 | 350 | 100 psig (689 kPaG) | 87.79 | 11.90 | 0.13 | 0.18 | 88.1 | 99.6 |
| 4 | 350 | 150 psig (1,034 kPaG) | 92.78 | 6.88 | 0.13 | 0.21 | 93.1 | 99.6 |
| 5 | 350 | 200 psig (1,379 kPaG) | 97.32 | 1.98 | 0.12 | 0.58 | 98.0 | 99.3 |
| 6 | 400 | 0 psig (kPaG) | | | | | 78 | 99 |
| 7 | 400 | 50 psig (345 kPaG) | 99.1 | 0.55 | 0.10 | 0.25 | 99.4 | 99.6 |
| 8 | 400 | 100 psig (689 kPaG) | 99.66 | 0.04 | 0.07 | 0.23 | 100 | 99.7 |
| 9 | 400 | 150 psig (1,034 kPaG) | 99.73 | 0.00 | 0.08 | 0.19 | 100 | 99.7 |
| 10 | 400 | 200 psig (1,379 kPaG) | 99.8 | 0.00 | 0.20 | 0.00 | 100 | 99.8 |
| 11 | 200 | 200 psig (1,379 kPaG) | | | | | 3 | |
| 12 | 250 | 200 psig (1,379 kPaG) | | | | | 16 | |
| 13 | 300 | 200 psig (1,379 kPaG) | | | | | 61 | |
| 14 | 350 | 200 psig (1,379 kPaG) | | | | | 97 | |
| 15 | 400 | 200 psig (1,379 kPaG) | | | | | 100 | |
| 16 | 200 | 0 psig (kPaG) | | | | | 0 | |
| 17 | 250 | 0 psig (kPaG) | | | | | 15 | |
| 18 | 300 | 0 psig (kPaG) | | | | | 22 | |
| 19 | 350 | 0 psig (kPaG) | | | | | 64 | |
| 20 | 400 | 0 psig (kPaG) | | | | | 79 | |

Example 10: Separation of Trifluoroiodomethane

In this Example, the separation of trifluoroiodomethane is described. A mixture containing about 85 wt. % trifluoroiodomethane, about 10 wt. % trifluoroacetyl iodide, and about 5 wt. % carbon monoxide can be charged into a distillation column. The distillation column can include a 10 gallon reboiler at a temperature of about 25° C., a 2-inch inside diameter 10-foot Pro-Pak® column from the Cannon Instrument Company, State College, Pa., and about 30 theoretical plates. The distillation column can be equipped Aspects Aspect 1 is a gas-phase process for producing trifluoroiodomethane, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a first catalyst at a first reaction temperature from about 25° C. to about 400° C. to produce an intermediate product stream comprising trifluoroacetyl iodide, and reacting the intermediate product stream in the presence of a second catalyst at a second reaction temperature from about 200° C. to about 600° C. to produce a final product stream comprising the trifluoroiodomethane.

Aspect 2 is the process of Aspect 1, wherein the step of reacting the reactant stream, the first reaction temperature is from about 40° C. to about 120° C.

Aspect 3 is the process of Aspect 1, wherein the step of reacting the reactant stream, the first reaction temperature is from about 70° C. to about 100° C.

Aspect 4 is the process of Aspect 1, wherein the step of reacting the reactant stream, the first reaction temperature is from about 80° C. to about 100° C.

Aspect 5 is the process of any of Aspects 1-4, wherein in the providing step, the reactant stream comprises less than about 500 ppm by weight of oxygen.

Aspect 6 is the process of any of Aspects 1-4, wherein in the providing step, the reactant stream comprises less than about 100 ppm by weight of oxygen.

Aspect 7 is the process of any of Aspects 1-4, wherein in the providing step, the reactant stream comprises less than about 10 ppm by weight of oxygen.

Aspect 8 is the process of any of Aspects 1-4, wherein in the providing step, the reactant stream comprises less than about 1 ppm by weight of oxygen.

Aspect 9 is the process of any of Aspects 1-8, wherein in the providing step, the hydrogen iodide comprises less than about 500 ppm by weight of water.

Aspect 10 is the process of any of Aspects 1-8, wherein in the providing step, the hydrogen iodide comprises less than about 100 ppm by weight of water.

Aspect 11 is the process of any of Aspects 1-8, wherein in the providing step, the hydrogen iodide comprises less than about 10 ppm by weight of water.

Aspect 12 is the process of any of Aspects 1-8, wherein in the providing step, the hydrogen iodide comprises less than about 1 ppm by weight of water.

Aspect 13 is the process of any of Aspects 1-12, wherein in the providing step, a mole ratio of the hydrogen iodide to the trifluoroacetyl halide is from about 0.1:1 to about 10:1.

Aspect 14 is the process of any of Aspects 1-12, wherein in the providing step, a mole ratio of the hydrogen iodide to the trifluoroacetyl halide is from about 0.5:1 to about 2.0:1.

Aspect 15 is the process of any of Aspects 1-12, wherein in the providing step, a mole ratio of the hydrogen iodide to the trifluoroacetyl halide is from about 0.6:1 to about 1.2:1.

Aspect 16 is the process of any of Aspects 1-12, wherein in the providing step, a mole ratio of the hydrogen iodide to the trifluoroacetyl halide is from about 0.7:1 to about 1.0:1.

Aspect 17 is the process of any of Aspects 1-16, wherein in the step of reacting the reactant stream, the first catalyst comprises activated carbon, meso carbon, stainless steel, nickel, nickel-chromium alloy, nickel-chromium-molybdenum alloy, nickel-copper alloy, copper, alumina, platinum, palladium, metal carbides, non-metal carbides or combinations thereof.

Aspect 18 is the process of any of Aspects 1-16, wherein the first catalyst comprises activated carbon, meso carbon, stainless steel, platinum on a support, palladium on a support, silicon carbide, or combinations thereof.

Aspect 19 is the process of any of Aspects 1-16, wherein the first catalyst comprises platinum on a support, palladium on a support, activated carbon, silicon carbide, or combinations thereof.

Aspect 20 is the process of any of Aspects 1-16, wherein the first catalyst comprises activated carbon or silicon carbide.

Aspect 21 is the process of any of Aspects 1-20, wherein in the step of reacting the reactant stream, the reactant stream may be in contact with the first catalyst for a contact time from about 0.1 seconds to about 300 seconds.

Aspect 22 is the process of any of Aspects 1-20, wherein in the step of reacting the reactant stream, the reactant stream may be in contact with the first catalyst for a contact time from about 5 seconds to about 60 seconds.

Aspect 23 is the process of any of Aspects 1-20, wherein in the step of reacting the reactant stream, the reactant stream may be in contact with the first catalyst for a contact time from about 10 seconds to about 40 seconds.

Aspect 24 is the process of any of Aspects 1-20, wherein in the step of reacting the reactant stream, the reactant stream may be in contact with the first catalyst for a contact time from about 15 seconds to about 35 seconds.

Aspect 25 is the process of any of Aspects 1-24, wherein in the step of reacting the reactant stream is at a pressure from about atmospheric pressure to about 300 psig (2,068 kPaG).

Aspect 26 is the process of any of Aspects 1-24, wherein in the step of reacting the reactant stream is at a pressure from about 5 psig (34 kPaG) to about 200 psig (1,379 kPaG).

Aspect 27 is the process of any of Aspects 1-24, wherein in the step of reacting the reactant stream is at a pressure from about 10 psig (69 kPaG) to about 150 psig (1,034 kPaG).

Aspect 28 is the process of any of Aspects 1-24, wherein in the step of reacting the reactant stream is at a pressure from about 20 psig (138 kPaG) to about 100 psig (689 kPaG).

Aspect 29 is the process of any of Aspects 1-28, wherein in the step of reacting the intermediate product stream, the second reaction temperature is from about 250° C. to about 500° C.

Aspect 30 is the process of any of Aspects 1-28, wherein in the step of reacting the intermediate product stream, the second reaction temperature is from about 300° C. to about 400° C.

Aspect 31 is the process of any of Aspects 1-28, wherein in the step of reacting the intermediate product stream, the second reaction temperature is from about 300° C. to about 350° C.

Aspect 32 is the process of any of Aspects 1-31, wherein in the step of reacting the intermediate product stream, the intermediate product stream may be in contact with the second catalyst for a contact time from about 0.1 seconds to about 300 seconds.

Aspect 33 is the process of any of Aspects 1-31, wherein in the step of reacting the intermediate product stream, the intermediate product stream may be in contact with the second catalyst for a contact time from about 1 seconds to about 60 seconds.

Aspect 34 is the process of any of Aspects 1-31, wherein in the step of reacting the intermediate product stream, the intermediate product stream may be in contact with the second catalyst for a contact time from about 2 seconds to about 50 seconds.

Aspect 35 is the process of any of Aspects 1-31, wherein in the step of reacting the intermediate product, the intermediate product stream may be in contact with the second catalyst for a contact time from about 3 seconds to about 30 seconds.

Aspect 36 is the process of any of Aspects 1-35, wherein in the step of reacting the intermediate product stream, the second catalyst comprises stainless steel, nickel, nickel-chromium alloy, nickel-chromium-molybdenum alloy, nickel-copper alloy, copper, alumina, silicon carbide, platinum, palladium, rhenium, activated carbon, meso carbon or combinations thereof.

Aspect 37 is the process of any of Aspects 1-35, wherein in the step of reacting the intermediate product stream, the second catalyst comprises activated carbon, about 0.1 wt. % to about 1 wt. % platinum on a support, about 0.1 wt. % to about 1 wt. % palladium on a support, about 0.1 wt. % to about 1 wt. % rhenium on a support, or combinations thereof.

Aspect 38 is the process of any of Aspects 1-35, wherein in the step of reacting the intermediate product stream, the second catalyst comprises activated carbon or about 0.3 wt. % to about 0.7 wt. % palladium on a support.

Aspect 39 is the process of any of Aspects 1-35, wherein in the step of reacting the intermediate product stream, the second catalyst comprises activated carbon.

Aspect 40 is the process of any of Aspects 1-35, wherein in the step of reacting the intermediate product stream, the second catalyst consists of surfaces of a reactor in contact with the intermediate product stream.

Aspect 41 is the process of any of Aspects 1-40, wherein the step of reacting the intermediate product stream is at a pressure from about 5 psig (34 kPaG) to about 300 psig (2,068 kPaG).

Aspect 42 is a gas-phase process for producing trifluoroiodomethane, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a first catalyst at a first reaction temperature from about 25° C. to about 400° C., at a pressure from about atmospheric pressure to about 300 psig (2,068 kPaG) for a first contact time of about 0.1 seconds to about 300 seconds to produce an intermediate product stream comprising trifluoroacetyl iodide, and reacting the intermediate product stream in the presence of a second catalyst at a second reaction temperature from about 200° C. to about 600° C. for a second contact time of about 0.1 seconds to about 300 seconds to produce a final product stream comprising the trifluoroiodomethane, wherein a mole ratio of the hydrogen iodide to the trifluoroacetyl halide is from about 0.1:1 to about 10:1, the first catalyst comprises activated carbon, meso carbon, stainless steel, nickel, nickel-chromium alloy, nickel-chromium-molybdenum alloy, nickel-copper alloy, copper, alumina, platinum, palladium, metal carbides, non-metal carbides or combinations thereof, the second catalyst comprises stainless steel, nickel, nickel-chromium alloy, nickel-chromium-molybdenum alloy, nickel-copper alloy, copper, alumina, silicon carbide, platinum, palladium, rhenium, activated carbon, meso carbon or combinations thereof.

Aspect 43 is a gas-phase process for producing trifluoroiodomethane, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a first catalyst at a first reaction temperature from about 40° C. to about 120° C., at a pressure from about 5 psig (34 kPaG) to about 200 psig (1,379 kPaG) for a first contact time of about 5 seconds to about 60 seconds to produce an intermediate product stream comprising trifluoroacetyl iodide, and reacting the intermediate product stream in the presence of a second catalyst at a second reaction temperature from about 250° C. to about 500° C. for a second contact time of about 1 second to about 60 seconds to produce a final product stream comprising the trifluoroiodomethane, wherein a mole ratio of the hydrogen iodide to the trifluoroacetyl halide is from about 0.5:1 to about 2:1, the first catalyst comprises activated carbon, meso carbon, stainless steel, platinum on a support, palladium on a support, silicon carbide, or combinations thereof, the second catalyst comprises activated carbon, about 0.1 wt. % to about 1 wt. % platinum on a support, about 0.1 wt. % to about 1 wt. % palladium on a support, about 0.1 wt. % to about 1 wt. % rhenium on a support, or combinations thereof.

Aspect 44 is a gas-phase process for producing trifluoroiodomethane, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a first catalyst at a first reaction temperature from about 70° C. to about 100° C., at a pressure from about 10 psig (69 kPaG) to about 150 psig (1,034 kPaG) for a first contact time of about 10 seconds to about 40 seconds to produce an intermediate product stream comprising trifluoroacetyl iodide, and reacting the intermediate product stream in the presence of a second catalyst at a second reaction temperature from about 300° C. to about 400° C. for a second contact time of about 2 seconds to about 50 seconds to produce a final product stream comprising the trifluoroiodomethane, wherein a mole ratio of the hydrogen iodide to the trifluoroacetyl halide is from about 0.6:1 to about 1.2:1, wherein the first catalyst comprises platinum on a support, palladium on a support, activated carbon, silicon carbide, or combinations thereof, the second catalyst comprises activated carbon or about 0.3 wt. % to about 0.7 wt. % palladium on a support.

Aspect 45 is a gas-phase process for producing trifluoroiodomethane, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a first catalyst at a first reaction temperature from about 80° C. to about 100° C., at a pressure from about 10 psig (69 kPaG) to about 150 psig (1,034 kPaG) for a first contact time of about 15 seconds to about 35 seconds to produce an intermediate product stream comprising trifluoroacetyl iodide, and reacting the intermediate product stream in the presence of a second catalyst at a second reaction temperature from about 300° C. to about 350° C. for a second contact time of about 3 seconds to about 30 seconds to produce a final product stream comprising the trifluoroiodomethane, wherein a mole ratio of the hydrogen iodide to the trifluoroacetyl halide is from about 0.7:1 to about 1.0:1, wherein the first catalyst comprises platinum on a support, palladium on a support, silicon carbide, or combinations thereof, the second catalyst comprises activated carbon.

Aspect 46 is the process of any of Aspects 42-47, wherein in the providing step, the reactant stream comprises less than about 500 ppm by weight of oxygen and the hydrogen iodide comprises less than about 500 ppm by weight of water.

Aspect 47 is the process of any of Aspects 42-47, wherein in the providing step, the reactant stream comprises less than about 100 ppm by weight of oxygen and the hydrogen iodide comprises less than about 100 ppm by weight of water.

Aspect 48 is the process of any of Aspects 42-47, wherein in the providing step, the reactant stream comprises less than about 10 ppm by weight of oxygen and the hydrogen iodide comprises less than about 10 ppm by weight of water.

Aspect 49 is the process of any of Aspects 42-47, wherein in the providing step, the reactant stream comprises less than about 1 ppm by weight of oxygen and the hydrogen iodide comprises less than about 1 ppm by weight of water.

Aspect 50 is the process of any of Aspects 1-49, wherein in the providing step, the trifluoroacetyl halide comprises trifluoroacetyl chloride.

Aspect 51 is the process of any of Aspects 1-50, wherein organic compounds in the intermediate product stream comprise, in GC area % of total organic compounds, from about 10% to about 99% trifluoroacetyl iodide, from about 1% to about 90% unreacted trifluoroacetyl halide, less than about 0.010% trifluoroiodomethane, and less than about 15% organic compounds other than trifluoroacetyl iodide, trifluoroacetyl halide, and trifluoroiodomethane.

Aspect 52 is the process of any of Aspects 1-50, wherein organic compounds in the intermediate product stream comprise, in GC area % of total organic compounds, from about 50% to about 99% trifluoroacetyl iodide, from about 1% to about 50% unreacted trifluoroacetyl halide, less than about 0.002% trifluoroiodomethane, and less than about 8% organic compounds other than trifluoroacetyl iodide, trifluoroacetyl halide, and trifluoroiodomethane.

Aspect 53 is the process of any of Aspects 1-50, wherein organic compounds in the intermediate product stream comprise, in GC area % of total organic compounds, from about 60% to about 99% trifluoroacetyl iodide, from about 1% to about 40% unreacted trifluoroacetyl halide, less than about 0.001% trifluoroiodomethane, and less than about 4% organic compounds other than trifluoroacetyl iodide, trifluoroacetyl halide, and trifluoroiodomethane.

Aspect 54 is the process of any of Aspects 1-50, wherein organic compounds in the intermediate product stream comprise, in GC area % of total organic compounds, from about 70% to about 99% trifluoroacetyl iodide, from about 1% to about 30% unreacted trifluoroacetyl halide, less than about 0.0005% trifluoroiodomethane, and less than about 2% organic compounds other than trifluoroacetyl iodide, trifluoroacetyl halide, and trifluoroiodomethane.

Aspect 55 is the process of any of Aspects 1-54, further comprising the additional steps of separating unreacted trifluoroacetyl halide from the intermediate product stream, returning the separated trifluoroacetyl halide to the reactant stream, separating unreacted hydrogen iodide from the intermediate product stream, returning the unreacted hydrogen iodide to the reactant stream, separating unreacted trifluoroacetyl iodide from the final product stream and returning the separated unreacted trifluoroacetyl iodide to the intermediate product stream.

Aspect 56 is a gas-phase process for producing trifluoroacetyl iodide, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, and reacting the reactant stream in the presence of a first catalyst at a reaction temperature from about 25° C. to about 400° C. to produce a product stream comprising the trifluoroacetyl iodide.

Aspect 57 is the process of Aspect 56, wherein the step of reacting the reactant stream, the reaction temperature is from about 40° C. to about 120° C.

Aspect 58 is the process of Aspect 56, wherein the step of reacting the reactant stream, the reaction temperature is from about 70° C. to about 100° C.

Aspect 59 is the process of Aspect 56, wherein the step of reacting the reactant stream, the reaction temperature is from about 80° C. to about 100° C.

Aspect 60 is the process of any of Aspects 56-59, wherein in the providing step, the reactant stream comprises less than about 500 ppm by weight of oxygen.

Aspect 61 is the process of any of Aspects 56-59, wherein in the providing step, the reactant stream comprises less than about 100 ppm by weight of oxygen.

Aspect 62 is the process of any of Aspects 56-59, wherein in the providing step, the reactant stream comprises less than about 10 ppm by weight of oxygen.

Aspect 63 is the process of any of Aspects 56-59, wherein in the providing step, the reactant stream comprises less than about 1 ppm by weight of oxygen.

Aspect 64 is the process of any of Aspects 56-63, wherein in the providing step, the hydrogen iodide comprises less than about 500 ppm by weight of water.

Aspect 65 is the process of any of Aspects 56-63, wherein in the providing step, the hydrogen iodide comprises less than about 100 ppm by weight of water.

Aspect 66 is the process of any of Aspects 56-63, wherein in the providing step, the hydrogen iodide comprises less than about 10 ppm by weight of water.

Aspect 67 is the process of any of Aspects 56-63, wherein in the providing step, the hydrogen iodide comprises less than about 1 ppm by weight of water.

Aspect 68 is the process of any of Aspects 56-67, wherein in the providing step, a mole ratio of the hydrogen iodide to the trifluoroacetyl halide is from about 0.1:1 to about 10:1.

Aspect 69 is the process of any of Aspects 56-67, wherein in the providing step, a mole ratio of the hydrogen iodide to the trifluoroacetyl halide is from about 0.5:1 to about 2.0:1.

Aspect 70 is the process of any of Aspects 56-67, wherein in the providing step, a mole ratio of the hydrogen iodide to the trifluoroacetyl halide is from about 0.6:1 to about 1.2:1.

Aspect 71 is the process of any of Aspects 56-67, wherein in the providing step, a mole ratio of the hydrogen iodide to the trifluoroacetyl halide is from about 0.7:1 to about 1.0:1.

Aspect 72 is the process of any of Aspects 56-71, wherein in the step of reacting the reactant stream, the catalyst comprises activated carbon, meso carbon, stainless steel, nickel, nickel-chromium alloy, nickel-chromium-molybdenum alloy, nickel-copper alloy, copper, alumina, platinum, palladium, metal carbides, non-metal carbides or combinations thereof.

Aspect 73 is the process of any of Aspects 56-71, wherein the catalyst comprises activated carbon, meso carbon, stainless steel, platinum on a support, palladium on a support, silicon carbide, or combinations thereof.

Aspect 74 is the process of any of Aspects 56-71, wherein the catalyst comprises platinum on a support, palladium on a support, activated carbon, silicon carbide, or combinations thereof.

Aspect 75 is the process of any of Aspects 56-71, wherein the catalyst comprises activated carbon or silicon carbide.

Aspect 75 is the process of any of Aspects 56-75, wherein in the step of reacting the reactant stream, the reactant stream may be in contact with the catalyst for a contact time from about 0.1 seconds to about 300 seconds.

Aspect 77 is the process of any of Aspects 56-75, wherein in the step of reacting the reactant stream, the reactant stream may be in contact with the catalyst for a contact time from about 5 seconds to about 60 seconds.

Aspect 78 is the process of any of Aspects 56-75, wherein in the step of reacting the reactant stream, the reactant stream may be in contact with the catalyst for a contact time from about 10 seconds to about 40 seconds.

Aspect 79 is the process of any of Aspects 56-75, wherein in the step of reacting the reactant stream, the reactant stream may be in contact with the catalyst for a contact time from about 15 seconds to about 35 seconds.

Aspect 80 is the process of any of Aspects 56-79, wherein in the step of reacting the reactant stream is at a pressure from about atmospheric pressure to about 300 psig (2,068 kPaG).

Aspect 81 is the process of any of Aspects 56-79, wherein in the step of reacting the reactant stream is at a pressure from about 5 psig (34 kPaG) to about 200 psig (1,379 kPaG).

Aspect 82 is the process of any of Aspects 56-79, wherein in the step of reacting the reactant stream is at a pressure from about 10 psig (69 kPaG) to about 150 psig (1,034 kPaG).

Aspect 83 is the process of any of Aspects 56-79, wherein in the step of reacting the reactant stream is at a pressure from about 20 psig (138 kPaG) to about 100 psig (689 kPaG).

Aspect 84 is a gas-phase process for producing trifluoroacetyl iodide, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a catalyst at a reaction temperature from about 25° C. to about 400° C., at a pressure from about atmospheric pressure to about 300 psig (2,068 kPaG) for a contact time of about 0.1 seconds to about 300 seconds to produce a product stream comprising the trifluoroacetyl iodide, wherein a mole ratio of the hydrogen iodide to the trifluoroacetyl halide is from about 0.1:1 to about 10:1, and the catalyst comprises activated carbon, meso carbon, stainless steel, nickel, nickel-chromium alloy, nickel-chromium-molybdenum alloy, nickel-copper alloy, copper, alumina, platinum, palladium, metal carbides, non-metal carbides or combinations thereof.

Aspect 85 is a gas-phase process for producing trifluoroacetyl iodide, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a catalyst at a reaction temperature from about 40° C. to about 120° C., at a pressure from about 5 psig (34 kPaG) to about 200 psig (1,379 kPaG) for a contact time of about 5 seconds to about 60 seconds to produce a product stream comprising trifluoroacetyl iodide, wherein a mole ratio of the hydrogen iodide to the trifluoroacetyl halide is from about 0.5:1 to about 2:1 and the catalyst comprises activated carbon, meso carbon, stainless steel, platinum on a support, palladium on a support, silicon carbide, or combinations thereof.

Aspect 86 is a gas-phase process for producing trifluoroacetyl iodide, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a catalyst at a reaction temperature from about 70° C. to about 100° C., at a pressure from about 10 psig (69 kPaG) to about 150 psig (1,034 kPaG) for a contact time of about 10 seconds to about 40 seconds to produce a product stream comprising trifluoroacetyl iodide, wherein a mole ratio of the hydrogen iodide to the trifluoroacetyl halide is from about 0.6:1 to about 1.2:1 and the catalyst comprises platinum on a support, palladium on a support, activated carbon, silicon carbide, or combinations thereof.

Aspect 87 is a gas-phase process for producing trifluoroacetyl iodide, the process comprising providing a reactant stream comprising hydrogen iodide and at least one trifluoroacetyl halide selected from the group consisting of trifluoroacetyl chloride, trifluoroacetyl fluoride, trifluoroacetyl bromide, and combinations thereof, reacting the reactant stream in the presence of a catalyst at a reaction temperature from about 80° C. to about 100° C., at a pressure from about 10 psig (69 kPaG) to about 150 psig (1,034 kPaG) for a contact time of about 15 seconds to about 35 seconds to produce a product stream comprising trifluoroacetyl iodide, wherein a mole ratio of the hydrogen iodide to the trifluoroacetyl halide is from about 0.7:1 to about 1.0:1 and the catalyst comprises platinum on a support, palladium on a support, silicon carbide, or combinations thereof.

Aspect 88 is the process of any of Aspects 84-87, wherein in the providing step, the reactant stream comprises less than about 500 ppm by weight of oxygen and the hydrogen iodide comprises less than about 500 ppm by weight of water.

Aspect 89 is the process of any of Aspects 84-87, wherein in the providing step, the reactant stream comprises less than about 100 ppm by weight of oxygen and the hydrogen iodide comprises less than about 100 ppm by weight of water.

Aspect 90 is the process of any of Aspects 84-87, wherein in the providing step, the reactant stream comprises less than about 10 ppm by weight of oxygen and the hydrogen iodide comprises less than about 10 ppm by weight of water.

Aspect 91 is the process of any of Aspects 84-87, wherein in the providing step, the reactant stream comprises less than about 1 ppm by weight of oxygen and the hydrogen iodide comprises less than about 1 ppm by weight of water.

Aspect 92 is the process of any of Aspects 56-91, wherein in the providing step, the trifluoroacetyl halide comprises trifluoroacetyl chloride.

Aspect 93 is a composition comprising at least 98 wt. % of trifluoroacetyl iodide, and from about 1 ppm to about 20,000 ppm (about 2 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 94 is a composition comprising at least 99 wt. % of trifluoroacetyl iodide, and from 1 ppm to 10,000 ppm (1 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 95 is a composition comprising at least 99.5 wt. % of trifluoroacetyl iodide, and from 1 ppm to 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 96 is a composition comprising at least 99.7 wt. % of trifluoroacetyl iodide, and from 1 ppm to 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 97 is a composition consisting essentially of at least 98 wt. % of trifluoroacetyl iodide, and from about 1 ppm to about 20,000 ppm (about 2 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 98 is a composition consisting essentially of at least 99 wt. % of trifluoroacetyl iodide, and from 1 ppm to 10,000 ppm (1 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 99 is a composition consisting essentially of at least 99.5 wt. % of trifluoroacetyl iodide, and from 1 ppm to 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 100 is a composition consisting essentially of at least 99.7 wt. % of trifluoroacetyl iodide, and from 1 ppm to 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 101 is a composition consisting of at least 98 wt. % of trifluoroacetyl iodide, and from about 1 ppm to about 20,000 ppm (about 2 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 102 is a composition consisting of at least 99 wt. % of trifluoroacetyl iodide, and from 1 ppm to 10,000 ppm (1 wt. %) in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 103 is a composition consisting of at least 99.5 wt. % of trifluoroacetyl iodide, and from 1 ppm to 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 104 is a composition consisting of at least 99.7 wt. % of trifluoroacetyl iodide, and from 1 ppm to 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

Aspect 105 is a composition comprising at least 99 wt. % of trifluoroiodomethane, from 1 ppm to 500 ppm chlorotrifluoroethane, less than 500 ppm hexafluoroethane, less than 500 ppm trifluoromethane, less than 100 ppm carbon monoxide, less than 1 ppm hydrogen chloride and from 1 ppm to 500 ppm in total of compounds selected from the group consisting of trifluoroacetyl fluoride, hexafluoropropanone, trifluoroacetaldehyde, and trifluoroacetyl chloride.

Aspect 106 is a composition comprising at least 99.5 wt. % of trifluoroiodomethane, from 1 ppm to 250 ppm chlorotrifluoroethane, less than 250 ppm hexafluoroethane, less than 250 ppm trifluoromethane, less than 50 ppm carbon monoxide, less than 0.5 ppm hydrogen chloride and from 1 ppm to 250 ppm in total of compounds selected from the group consisting of trifluoroacetyl fluoride, hexafluoropropanone, trifluoroacetaldehyde, and trifluoroacetyl chloride.

Aspect 107 is a composition comprising at least 99.7 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and from 1 ppm to 100 ppm in total of compounds selected from the group consisting of trifluoroacetyl fluoride, hexafluoropropanone, trifluoroacetaldehyde, and trifluoroacetyl chloride.

Aspect 108 is a composition comprising at least 99.9 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and from 1 ppm to 100 ppm in total of compounds selected from the group consisting of trifluoroacetyl fluoride, hexafluoropropanone, trifluoroacetaldehyde, and trifluoroacetyl chloride.

Aspect 109 is a composition consisting essentially of at least 99 wt. % of trifluoroiodomethane, from 1 ppm to 500 ppm chlorotrifluoroethane, less than 500 ppm hexafluoroethane, less than 500 ppm trifluoromethane, less than 100 ppm carbon monoxide, less than 1 ppm hydrogen chloride and from 1 ppm to 500 ppm in total of compounds selected from the group consisting of trifluoroacetyl fluoride, hexafluoropropanone, trifluoroacetaldehyde, and trifluoroacetyl chloride.

Aspect 110 is a composition consisting essentially of at least 99.5 wt. % of trifluoroiodomethane, from 1 ppm to 250 ppm chlorotrifluoroethane, less than 250 ppm hexafluoroethane, less than 250 ppm trifluoromethane, less than 50 ppm carbon monoxide, less than 0.5 ppm hydrogen chloride and from 1 ppm to 250 ppm in total of compounds selected from the group consisting of trifluoroacetyl fluoride, hexafluoropropanone, trifluoroacetaldehyde, and trifluoroacetyl chloride.

Aspect 111 is a composition consisting essentially of at least 99.7 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and from 1 ppm to 100 ppm in total of compounds selected from the group consisting of trifluoroacetyl fluoride, hexafluoropropanone, trifluoroacetaldehyde, and trifluoroacetyl chloride.

Aspect 112 is a composition consisting essentially of at least 99.9 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and from 1 ppm to 100 ppm in total of compounds selected from the group consisting of trifluoroacetyl fluoride, hexafluoropropanone, trifluoroacetaldehyde, and trifluoroacetyl chloride.

Aspect 109 is a composition consisting of at least 99 wt. % of trifluoroiodomethane, from 1 ppm to 500 ppm chlorotrifluoroethane, less than 500 ppm hexafluoroethane, less than 500 ppm trifluoromethane, less than 100 ppm carbon monoxide, less than 1 ppm hydrogen chloride and from 1 ppm to 500 ppm in total of compounds selected from the group consisting of trifluoroacetyl fluoride, hexafluoropropanone, trifluoroacetaldehyde, and trifluoroacetyl chloride.

Aspect 110 is a composition consisting of at least 99.5 wt. % of trifluoroiodomethane, from 1 ppm to 250 ppm chlorotrifluoroethane, less than 250 ppm hexafluoroethane, less than 250 ppm trifluoromethane, less than 50 ppm carbon monoxide, less than 0.5 ppm hydrogen chloride and from 1 ppm to 250 ppm in total of compounds selected from the group consisting of trifluoroacetyl fluoride, hexafluoropropanone, trifluoroacetaldehyde, and trifluoroacetyl chloride.

Aspect 111 is a composition consisting of at least 99.7 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and from 1 ppm to 100 ppm in total of compounds selected from the group consisting of trifluoroacetyl fluoride, hexafluoropropanone, trifluoroacetaldehyde, and trifluoroacetyl chloride.

Aspect 112 is a composition consisting of at least 99.9 wt. % of trifluoroiodomethane, from 1 ppm to 100 ppm chlorotrifluoroethane, less than 100 ppm hexafluoroethane, less than 100 ppm trifluoromethane, less than 20 ppm carbon monoxide, less than 0.2 ppm hydrogen chloride and from 1 ppm to 100 ppm in total of compounds selected from the group consisting of trifluoroacetyl fluoride, hexafluoropropanone, trifluoroacetaldehyde, and trifluoroacetyl chloride.

Aspect 113 is a gas-phase process for producing trifluoroiodomethane, the process comprising providing a reactant stream comprising trifluoroacetyl iodide, and reacting the reactant stream in the presence of a catalyst at a reaction temperature from about 200° C. to about 600° C. to produce a product stream comprising the trifluoroiodomethane.

Aspect 114 is the process of Aspect 113, wherein in the step of reacting the reactant stream, the reaction temperature is from about 250° C. to about 500° C.

Aspect 115 is the process of Aspect 113, wherein in the step of reacting the reactant stream, the reaction temperature is from about 300° C. to about 400° C.

Aspect 116 is the process of Aspect 113, wherein in the step of reacting the reactant stream, the reaction temperature is from about 300° C. to about 350° C.

Aspect 117 is the process of any of Aspects 113-116, wherein in the step of reacting the reactant stream, the reactant stream may be in contact with the catalyst for a contact time from about 0.1 seconds to about 300 seconds.

Aspect 118 is the process of any of Aspects 113-116, wherein in the step of reacting the reactant stream, the reactant stream may be in contact with the catalyst for a contact time from about 1 seconds to about 60 seconds.

Aspect 119 is the process of any of Aspects 113-116, wherein in the step of reacting the reactant stream, the reactant stream may be in contact with the catalyst for a contact time from about 2 seconds to about 50 seconds.

Aspect 120 is the process of any of Aspects 113-116, wherein in the step of reacting the reactant stream, the reactant stream may be in contact with the catalyst for a contact time from about 3 seconds to about 30 seconds.

Aspect 121 is the process of any of Aspects 113-120, wherein in the step of reacting the reactant stream, the catalyst comprises stainless steel, nickel, nickel-chromium alloy, nickel-chromium-molybdenum alloy, nickel-copper alloy, copper, alumina, silicon carbide, platinum, palladium, rhenium, activated carbon, meso carbon or combinations thereof.

Aspect 122 is the process of any of Aspects 113-120, wherein in the step of reacting the reactant stream, the catalyst comprises activated carbon, about 0.1 wt. % to about 1 wt. % platinum on a support, about 0.1 wt. % to about 1 wt. % palladium on a support, about 0.1 wt. % to about 1 wt. % rhenium on a support, or combinations thereof.

Aspect 123 is the process of any of Aspects 113-120, wherein in the step of reacting the reactant stream, the catalyst comprises activated carbon or about 0.3 wt. % to about 0.7 wt. % palladium on a support.

Aspect 124 is the process of any of Aspects 113-120, wherein in the step of reacting the reactant stream, the catalyst comprises activated carbon.

Aspect 125 is the process of any of Aspects 113-120, wherein in the step of reacting the reactant stream, the catalyst consists of surfaces of a reactor in contact with the reactant stream.

Aspect 126 is the process of any of Aspects 113-125, wherein the step of reacting the reactant stream is at a pressure from about 5 psig (34 kPaG) to about 300 psig (2,068 kPaG).

Aspect 127 is a gas-phase process for producing trifluoroiodomethane, the process comprising providing a reactant stream comprising trifluoroacetyl iodide, and reacting the reactant stream in the presence of a catalyst at a reaction temperature from about 200° C. to about 600° C. for a contact time of about 0.1 seconds to about 300 seconds to produce a product stream comprising the trifluoroiodomethane, wherein the catalyst comprises stainless steel, nickel, nickel-chromium alloy, nickel-chromium-molybdenum alloy, nickel-copper alloy, copper, alumina, silicon carbide, platinum, palladium, rhenium, activated carbon, meso carbon or combinations thereof.

Aspect 128 is a gas-phase process for producing trifluoroiodomethane, the process comprising providing a reactant stream comprising trifluoroacetyl iodide, and reacting the reactant stream in the presence of a catalyst at a reaction temperature from about 250° C. to about 500° C. for a contact time of about 1 second to about 60 seconds to produce a product stream comprising the trifluoroiodomethane, wherein the catalyst comprises activated carbon, about 0.1 wt. % to about 1 wt. % platinum on a support, about 0.1 wt. % to about 1 wt. % palladium on a support, about 0.1 wt. % to about 1 wt. % rhenium on a support, or combinations thereof.

Aspect 129 is a gas-phase process for producing trifluoroiodomethane, the process comprising providing a reactant stream comprising trifluoroacetyl iodide, and reacting the reactant stream in the presence of a catalyst at a reaction temperature from about 300° C. to about 400° C. for a contact time of about 2 seconds to about 50 seconds to produce a product stream comprising the trifluoroiodomethane, wherein the catalyst comprises activated carbon or about 0.3 wt. % to about 0.7 wt. % palladium on a support.

Aspect 130 is a gas-phase process for producing trifluoroiodomethane, the process comprising providing a reactant stream comprising trifluoroacetyl iodide, and reacting the reactant stream in the presence of a catalyst at a reaction temperature from about 300° C. to about 350° C. for a contact time of about 3 seconds to about 30 seconds to produce a product stream comprising the trifluoroiodomethane, wherein the catalyst comprises activated carbon.

What is claimed is:
1. A composition comprising:
at least 99 wt. % of trifluoroiodomethane;
less than 500 ppm hexafluoroethane;
less than 500 ppm trifluoromethane;
less than 100 ppm carbon monoxide;
less than 1 ppm hydrogen chloride; and
from 1 ppm to 500 ppm in total of compounds selected from the group consisting of trifluoroacetyl fluoride, hexafluoropropanone, trifluoroacetaldehyde, and trifluoroacetyl chloride.
2. The composition of claim 1 comprising:
at least 99.5 wt. % of trifluoroiodomethane;
less than 250 ppm hexafluoroethane;
less than 250 ppm trifluoromethane;

less than 50 ppm carbon monoxide;
less than 0.5 ppm hydrogen chloride; and
from 1 ppm to 250 ppm in total of compounds selected from the group consisting of trifluoroacetyl fluoride, hexafluoropropanone, trifluoroacetaldehyde, and trifluoroacetyl chloride.

3. The composition of claim 1 comprising:
at least 99.7 wt. % of trifluoroiodomethane;
less than 100 ppm hexafluoroethane;
less than 100 ppm trifluoromethane;
less than 20 ppm carbon monoxide;
less than 0.2 ppm hydrogen chloride; and
from 1 ppm to 100 ppm in total of compounds selected from the group consisting of trifluoroacetyl fluoride, hexafluoropropanone, trifluoroacetaldehyde, and trifluoroacetyl chloride.

4. The composition of claim 1 comprising:
at least 99.9 wt. % of trifluoroiodomethane;
less than 100 ppm hexafluoroethane;
less than 100 ppm trifluoromethane;
less than 20 ppm carbon monoxide;
less than 0.2 ppm hydrogen chloride; and
from 1 ppm to 100 ppm in total of compounds selected from the group consisting of trifluoroacetyl fluoride, hexafluoropropanone, trifluoroacetaldehyde, and trifluoroacetyl chloride.

5. A composition comprising:
at least 98 wt. % of trifluoroacetyl iodide, and
from about 1 ppm to about 20,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

6. The composition of claim 5 consisting essentially of:
at least 98 wt. % of trifluoroacetyl iodide, and
from about 1 ppm to about 20,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

7. The composition of claim 5 comprising:
at least 99 wt. % of trifluoroacetyl iodide, and
from about 1 ppm to about 10,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

8. The composition of claim 7 consisting essentially of:
at least 99 wt. % of trifluoroacetyl iodide, and
from about 1 ppm to about 10,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

9. The composition of claim 5 comprising:
at least 99.5 wt. % of trifluoroacetyl iodide, and
from about 1 ppm to about 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

10. The composition of claim 9 consisting essentially of:
at least 99.5 wt. % of trifluoroacetyl iodide, and
from about 1 ppm to about 5,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

11. The composition of claim 5 comprising:
at least 99.7 wt. % of trifluoroacetyl iodide, and
from about 1 ppm to about 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

12. The composition of claim 11 consisting essentially of:
at least 99.7 wt. % of trifluoroacetyl iodide, and
from about 1 ppm to about 3,000 ppm in total of compounds selected from the group consisting of chlorotrifluoroethane, trifluoroacetyl chloride, iodotrifluoromethane, trifluoroacetyl fluoride, hexafluoropropanone, trifluoroacetic acid and chlorotrifluoromethane.

\* \* \* \* \*